United States Patent [19]

Keyes et al.

[11] Patent Number: 4,609,625
[45] Date of Patent: Sep. 2, 1986

[54] PROCESS FOR THE PRODUCTION OF MODIFIED PROTEINS AND PRODUCT THEREOF

[75] Inventors: Melvin H. Keyes, Sylvania; Saraswathi Vasan, Toledo, both of Ohio

[73] Assignee: Owens-Illinois, Inc., Toledo, Ohio

[21] Appl. No.: 551,632

[22] Filed: Nov. 14, 1983

[51] Int. Cl.[4] .................. C12N 11/14; C12N 11/02; C12N 11/10; C12N 11/08; C12N 11/06; C12N 9/96; C12N 9/00; C12N 9/16; C12N 9/90; C12N 9/92; C07K 3/08; C07K 17/00

[52] U.S. Cl. ................... 435/176; 435/177; 435/178; 435/180; 435/181; 435/188; 435/183; 435/196; 435/233; 435/234; 525/54.1; 530/815; 530/402

[58] Field of Search ............... 435/183, 184, 188, 189, 435/200, 201, 203, 190, 223, 178, 179, 176, 232, 234, 233; 260/112 R; 525/54.1

[56] References Cited

U.S. PATENT DOCUMENTS 4,206,286  6/1980  Keyes ................................ 435/190
4,366,030  5/1981  Tschang et al. .................... 435/188

OTHER PUBLICATIONS

Yamauchi, et al., Reversible Conversion of Lysime Monooxygenase to an Oxidase; *J. of Biol. Chem.*, vol. 248, 1973, pp. 3750–3752.
Mahler, et al., *Biological Chemistry*, 1966, Harper and Row, N.Y., pp. 287–295.
Beaven et al., *International Journal of Peptide Research*, vol. 5, pp. 215–218, 1973.

*Primary Examiner*—Lionel M. Shapiro
*Attorney, Agent, or Firm*—John R. Nelson

[57] ABSTRACT

A process is disclosed for chemically modifying naturally occurring proteins to produce enzyme-like modified proteins. The process comprises partially denaturing a cofactor containing holoprotein by removal of the cofactor to produce a partially denatured cofactorless or so-called apoprotein. The partially denatured protein is contacted with an inhibitor of a selected model enzyme and cross-linked. The resultant protein product is an enzyme-like modified protein having the catalytic characteristics of the model enzyme whose inhibitor is contacted with the partially denatured apoprotein.

18 Claims, 5 Drawing Figures

PLOT OF △ ABS. VS TIME FOR (DIALYZED)
ENZYME-LIKE MODIFIED PROTEIN
SLOPE = $3.33 \times 10^{-4}$ ABS/MIN
ACT. = 3.9 U/G
pH OF ASSAY = 8.0

PLOT OF △ ABS. VS. TIME FOR GLUCOSE
ISOMERASE-LIKE MODIFIED PROTEIN
SLOPE = $5.96 \times 10^{-4}$ ABS/MIN
ACTIVITY = 5.3 U/GRAM pH VERSUS GLUCOSE ISOMERASE
ACTIVITY OF MODIFIED CONCANAVALIN A
GLUTARALDEHYDE CROSS-LINKED pH VERSUS GLUCOSE ISOMERASE ACTIVITY OF
MODIFIED CONCANAVALIN A
SUBERIMIDATE CROSS-LINKED

PROCESS FOR THE PRODUCTION OF MODIFIED PROTEINS AND PRODUCT THEREOF

BACKGROUND OF THE INVENTION

1. Field of the Invention

Proteins are biologically synthesized macromolecules having various roles in living systems. Enzymes are particular varieties of biologically-active proteins which catalyze specific reactions. Presently, enzyme technology is used in many areas in industry and research, such as, for example, medical research, food processing and preservation, the production of fermented beverages, the production of pharmaceuticals and the analytical determination of the concentration of various metabolites and food components by analytical enzyme techniques.

Enzymes are highly specific in their biological activity and generally catalyze a particular reaction at a very high rate compared to the corresponding reaction occurring at room temperature without biological catalysis. One enzyme may show catalytic activity with respect to a number of substrates upon which it can act. Accordingly, a given enzyme may catalyze the synthesis or degradation of more than one substrate. Some proteins which are not considered classical enzymes, such as bovine serum albumin, show very limited catalytic activity with respect to one or more substrates.

Many enzymes are found in nature in very small quantities. Accordingly, their isolation, purification and use is limited to a small scale operation in view of the expense and time needed to isolate them in a useful form.

Some enzymes occur in nature in relatively large quantities and are relatively easy to isolate, purify and use. Unfortunately, due to the precise catalytic behavior of enzymes, the enzymes available in large quantities can only catalyze certain select reactions. Moreover, many nonenzymatic proteins are available in large supply at low cost in pure form. In the past, these proteins have been useless as catalysts.

Much effort has been directed in the recent past toward the preparation of partially or totally synthetic catalysts which exhibit catalytic behavior similar to the catalytic behavior exhibited by biocatalysts, namely the native enzymes. Many biocatalysts or enzymes are either scarce or expensive to isolate, thus the attempts to mimic their catalytic activity. Further, some attempts have been made to modify native enzymes to change their enzymatic specificity so that they may function to catalyze a reaction which they previously could not catalyze.

2. Description of the References

One technique known to achieve enzyme-like behavior to catalyze a specific reaction is the synthesis of so called enzyme model molecules. For example, low molecular weight compounds may be covalently bonded to functional groups which exhibit the activity of the active site of an enzyme. Examples of such preparations are described in the publications: Breslow, R., *Advances in Chemistry Series*, R. F. Gould, Ed., American Chemical Society, Washington, D. C. 21–43 (1971) and Tang, C. C.; Davilian, D.; Haung, P. and Breslow, R., *J. Amer. Chem. Soc.*, 100, 3918 (1978) and Breslow, R., Doherty, J., Guillot, G. and Lipsey, C., *J. Amer. Chem. Soc.*, 100, 3227 (1978).

Another technique involves the use of a synthetic polymer matrix which is modified along its backbone to provide functional groups which exhibit the function of the active site of a given enzyme. Examples of such techniques can be found in the following articles: Wulff, G. and Schulza, I., *Israel J. Chem.*, 17, 291 (1978) and Suh, J. and Klotz, I. M., *Bioorganic*, 6, 165 (1977).

Another technique involves the attachment of a new chemical moiety to a native enzyme near the active site of the enzyme to attempt to cause the enzyme to react with a different catalytic activity. One example of this is the conversion of papain, a proteolytic enzyme to an oxidase type enzyme by the covalent attachment of a flavin near the active site of the native papain enzyme, as illustrated in the articles: Levine, H. L. and Kaiser, E. T., *J. Amer. Chem. Soc.*, 100, 7670 (1978); Kaiser, E. T., et al., *Adv. in Chemistry Series*, No. 191, Biomimetic Chemistry, 1980; and Otsuki, T.; Nakagawa, Y. and Kaiser, E. T., *J. C. S. Chem. Comm.*, 11,457 (1978). Other examples of such enzymatic modification may be found in the article: Wilson, M. E. and Whitesides, G. M., *J. Amer. Chem. Soc.*, 100, 306 (1978).

Still another attempt to change enzyme specificity is the immobilization of a native enzyme into a gel matrix. For example, trypsin enzyme has been immobilized in polyacrylamide gel. The polyacrylamide gel allows amino acid esters to diffuse through the gel matrix to react with the enzyme but will not allow larger proteins to diffuse through. Thus, the enzyme specificity is changed by eliminating access of one of the substrate molecules to the enzyme.

Also, it is known that a native lysine mono-oxygenase can be reacted to block the sulfhydryl groups on the enzyme. When the specific enzyme lysine mono-oxygenase is so treated, it shows modified catalytic activity toward amino acids and catalyses oxidative deamination instead of its natural oxygenative decarboxylation. However, the reporters cannot account for the modified behavior. See the article by Yamauchi, T.; Yamamoto, S. and Hayaishi, O., in *The Journal of Biological Chemistry*, 248, 10, 3750–3752 (1973).

Also, it has been reported that by reacting a native enzyme, for example trypsin, with its known inhibitor, and subsequently cross-linking the enzyme, its activity with respect to its typical substrates can be modified. See the article by Beaven, G. H. and Gratzer, W. B. in *Int. J. Peptide Res.*, 5, 215–18 (1973).

Also, synthetic proteins have been synthesized by the anchoring of an amino acid residue on a solid support and subsequently adding amino acid residues one after another.

Further, semisynthetic proteins have been synthesized by a method wherein a native protein is subjected to limited hydroysis to produce protein fragments. The fragments of the native protein are then subjected to a process whereby one or more amino acid residues are added or removed from the fragments to form modified fragments. The resultant modified fragments are then reattached to form the semisynthetic protein with an altered amino acid residue composition. Examples of the synthetic and semisynthetic protein technologies cited immediately above are found in the book *Semisynthetic Proteins* by R. E. Offord, published by John Wiley and Sons, Ltd., copyrighted in 1980.

While these techniques are suitable for many applications, a need exists for a simple, efficient, economical and systematic method for chemically modifying an inexpensive and commercially availble native protein to produce an enzyme-like modified protein. The protein can show a catalytic enzymatic activity with respect to a desired chemical reaction which was not previously a commercially-useful reaction catalyzed by the native enzyme and which new reaction can be predetermined in a systematic fashion. The methods disclosed in the above-disclosed references simply subject an enzyme to a set of conditions and attempt to elucidate its behavior.

SUMMARY OF THE INVENTION

The present invention achieves an enzyme-like modified protein by converting a naturally occurring protein starting material or so-called native protein to an enzyme-like modified protein exhibiting different characteristics than the native protein starting material.

According to the present invention, a cofactor containing native protein is partially denatured by the removal of its naturally occurring cofactor to produce the corresponding apoprotein. Next, the partially denatured apoprotein is admixed with an inhibitor for the predetermined model enzyme, whose activity is to be modeled.

Next, the partially denatured apoprotein, in the presence of the inhibitor of the model enzyme, is cross-linked to define a new enzyme-like modified protein conformation which is defined by the inhibitor of the model enzyme and is preserved by the cross-linking.

Subsequently, the inhibitor of the model enzyme and any excess cross-linking agent are removed from the newly formed, cofactorless enzyme-like modified protein to yield a functional, analogue to the model enzyme. The modified cofactorless protein thusly produced exhibits activity characteristic of the model enzyme.

BRIEF DESCRIPTION OF THE DRAWINGS

The details of the invention will be described in the accompanying specification in view of the drawings, in which.

DETAILED DESCRIPTION OF THE INVENTION

Figure 1:
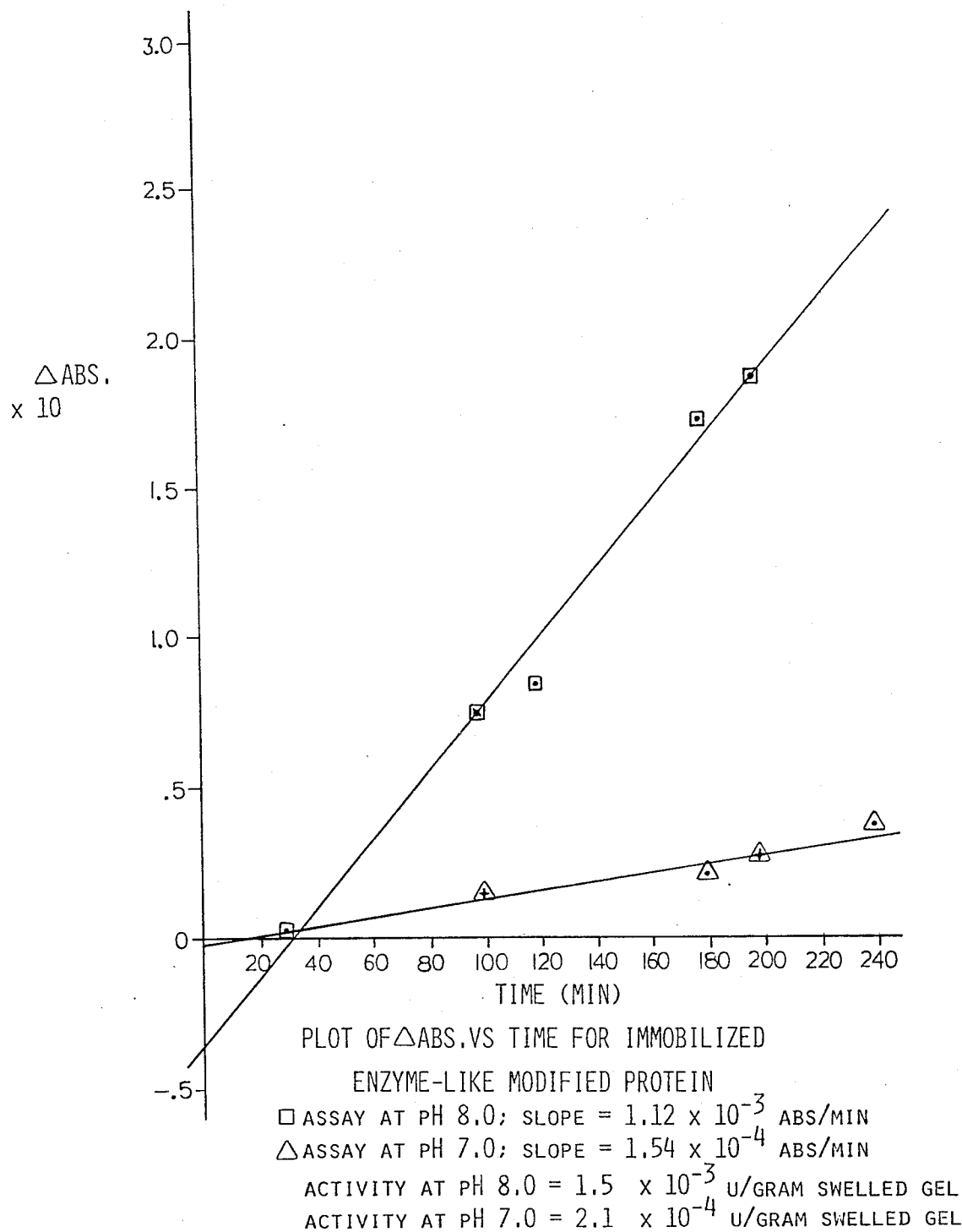
FIG. 1 illustrates the catalytic activity of the immobilized enzyme-like modified protein prepared in Example 2.

In attaining the advantages of the present invention, it has now been discovered that a cofactor containing protein can be modified from its native conformation to a modified conformation by practicing the process of the present invention. The new conformational state defines an enzyme-like modified protein having catalytic activity.

As used herein, the word "enzyme" is defined as a protein which has well-known catalytic activity toward specific substrates. The term "protein" as used herein is defined as generally accepted in the art, to wit, a polypeptide formed of amino acids to yield a biological molecule.

The process of the present invention comprises chemically modifying a native cofactor containing protein from one conformation, its natural or native state, to a second conformation, a new modified state. The process produces a new, cofactorless, enzyme-like modified protein which models one or more of the enzymatic activity characteristics of the selected model enzyme. We have discovered that a cofactor containing native protein can be converted to a cofactorless enzyme-like modified protein without any substantial adverse effects upon the protein during the conversion process. No adverse steric or other structural problems militate against the preparation of a new cofactorless enzyme-like modified protein when following our new process. It has also been discovered that enzyme-like activity can be generated in the cofactorless modified protein from either enzymatic proteins or nonenzymatic proteins. Thus the specificity of a naturally occurring enzyme can be changed or a catalytic activity can be induced into a nonenzymatic protein by practicing the process of the present invention.

In the preferred embodiment of the invention, a native cofactor containing protein is selected which is to be chemically modified by the present invention to produce the new cofactorless enzyme-like modified protein analogue of a desired naturally occurring model enzyme. The process of the present invention converts the cofactor dependant native protein, which does not possess any catalytic activity or the desired catalytic activity, namely, the enzymatic catalysis behavior of the model enzyme, into a cofactorless enzyme-like modified protein which mimics or copies the biological catalytic activity characteristics of the model enzyme.

A preferred way of carrying out the novel process of the present invention for chemically modifying a cofactor containing native protein to produce a predetermined cofactorless enzyme-like modified protein comprises the steps of: partially denaturing the cofactor containing native protein by removing the cofactor from the native protein structure; contacting the cofactorless partially denatured protein with an inhibitor for the predetermined model enzyme; and cross-linking the cofactorless partially denatured protein-inhibitor complex to form the new cofactorless enzyme-like modified protein. The cross-linking may be done simultaneous with the binding of the inhibitor to the partially denatured cofactorless protein or may be done as a separate step subsequent to the binding of the inhibitor to the partially denatured cofactorless protein. Any excess cross-linking agent and the inhibitor are removed from the newly created cofactorless enzyme-like modified protein to isolate the new catalytically active enzyme-like modified product protein. Gel chromatography, dialysis or any equivalent technique can be used to remove the inhibitor and excess cross-linking agent.

As defined herein, cofactor means a metal, non-protein organic or organo-metallic moiety required to lend natural biological activity to a native holoprotein wherein the metal, non-protein organic or organo-metallic moiety is covalently or non-covalently bound to the native holoprotein and specifically includes coenzymes, including prosthetic groups, and metal activators. Generally, coenzymes and prosthetic groups are organic or organo-metallic while activators are metal ions.

Examples of coenzymes and prosthetic groups include: FAD, FMN, NAD, NADP, ascorbic acid, biotin, biocytin, cobamide, coenzyme A, coenzyme Q, iron-protoporphyrin, pyridoxal phosphate, 6,8-dithio-n-octanoic acid, lipoic acid, lipoamide, tetrahydrofolate coenzymes, thiamine pyrophosphate, ubiquinone and cobamide coenzyme and others as defined in White, A., Handler, P., Smith, E. in "Principles of Biochemistry" Fifth Edition (1973) p. 215-216.

Examples of metal ion activators include:

$Mg^{+2}$, $Ca^{+2}$, $Co^{+2}$, $Mn^{+2}$, $Fe^{+2}$, $Fe^{+3}$, $Cu^{+2}$, $K^+$, $Na^+$ and $Zn^{+2}$.

As defined herein and as conventional in the art, apoprotein means a native protein which lacks its naturally occurring cofactor.

As used herein, the phrase "partial denaturation" means a change in the conformation of a protein so as to perturb the natural shape or conformation of the protein without causing the irreversable, gross denaturation of the protein. As used herein, the word "conformation" is defined as generally accepted in the art, to wit, that combination of secondary and tertiary amino acid structure which produces a characteristic protein shape.

The partial denaturation of the cofactor containing native protein is achieved herein by the removal of the cofactor. The cofactor may be removed by a number of processes.

Cofactor may be removed by a number of methods, depending on the nature of the cofactor and the tightness of binding. Some of the generally used procedures for cofactor removal are: acid ammonium sulfate precipitation (as disclosed by Husain, M. and Massey, V. (1978): Methods in Enzyology, Vol. 53, Part D, S. Fleischer and L. Packer ed. Academic Press, NY, 1978, p. 429-437); use of denaturing agent (Husain, above); reaction with cofactor binding reagents (as disclosed by Nihara, T., Toraya, T., and Fukui, S., (1981) J. Appl. Biochem. 212-217); treatment with acid and dialysis against EDTA (as disclosed by Becker, J. W., Reeke, G. N., Cunningham, B. A. and Edelman, G. M. (1976) Nature, 406-409); and by acid-acetone treatment (as disclosed by White, A., Handler, P., and Smith, E. L., in "Principles in Biochemistry" (1973) McGraw-Hill Book Co., p. 179).

As used herein, the term "inhibitor" means any compound with sufficient structural similarity to the natural substrate of a model enzyme to serve as a template for the catalytic site of the enzyme-like modified protein. In the preferred embodiment of the preparation of an enzyme-like modified protein, the inhibitor is any of the known classical inhibitors for a given model enzyme. However, as used herein "inhibitor" can include any molecule with sufficient structural similarity to the classical inhibitor to preserve an inhibitor-like site on the modified protein. The natural substrate of the model enzyme can act as the inhibitor or template for the modified protein in many cases. Inhibitors are generally not degraded by the enzyme, as are substrates, and serve to more readily preserve a catalytic site than the natural substrate. One example of the structural similarity of an enzyme inhibitor and the natural substrate of an enzyme is the case of glucose oxidase. Glucose is the natural substrate of glucose oxidase while D-glucal is the inhibitor for glucose oxidase. Glucose and D-glucal are very structurally similar.

As used herein, the term "cross-linking" means the formation of covalent bonds between reactive sites on a protein. Generally, protein cross-linking is accomplished by the use of multifunctional reagents such as glutaraldehyde. Other examples of suitable cross-linking reagents to effect the cross-linking of a protein are: 2-amino-4, 6-dichloro-s-triazine; diazonium salts; N-hydroxysuccinamide; p-benzoylazide, suberimidate and those reagents disclosed in the following references: Wold, F., Methods Enzymol, 11, edited by Hirs, C. H. W., Academic Press, 617, (1967); Fasold, H. et al., Augen. Chem. Int. Ed. Engl., 10, 795, (1971); and Goldstein, L. and G. Manecke, Applied Biochemistry and Bioengineering, I, L. Wingard, E. KatchalskiKatzir, and L. Goldstein eds, Academic Press, 34-41 (1976).

In an alternative embodiment of cross-linking of the partially denatured cofactorless protein, the cross-linking of the protein after it has been partially denatured and subjected to inhibitor contact may be achieved by disulphide rearrangement when the native protein being converted to an enzyme-like modified cofactorless protein analogue of a model enzyme is rich in disulphide bridges. Such disulphide rearrangement is accomplished by subjecting the native disulphide bridge rich protein, at about neutral pH, to various reagents to break the disulphide bridges to yield sulphydryl groups. A preferred reagent is beta-mercaptoethanol. The beta-mercaptoethanol cleaves the disulphide bridges, thereby loosening the conformational structure of the protein and further partially denaturing the protein by the formation of free sulphydryl groups. After the cofactorless protein has been contacted with the inhibitor of the model enzyme, the sulphydryl groups may be oxidized to the disulphide form to relink the cofactorless protein into a new, cofactorless enzyme-like modified protein.

Of course, the resultant disulphide rearranged enzyme-like modified protein may be further cross-linked to further stabilize the structure by reaction with the above-described cross-linking agents, like glutaraldehyde.

The relinking of sulphydryl groups in disulphides may be easily accomplished by raising the sulphydryl containing protein to an elevated pH. A pH value of between 9 and 10 is usually quite acceptable. It should be noted, however, that molecular oxygen is usually a reactant in a sulphydryl reaction to form disulphide bridges so the high pH reaction should be carried out in the presence of molecular oxygen. Other oxidizing agents which are known to oxidize sulphydryl functions to the corresponding disulphide are equally operative.

In one embodiment of the invention, a native or host cofactor-containing protein showing little or no catalytic activity, which requires one or more cofactors to perform its non-catalytic biological function, is converted chemically by the process of the present invention into a cofactorless enzyme-like modified protein analogue of a model enzyme.

Alternatively, a cofactor dependent enzyme, for example glucose oxidase, of the oxido-reductase family, can be converted by the process of the present invention into a cofactorless glucose isomerase-like modified protein. Glucose isomerase is a member of the isomerase family. Naturally occurring glucose isomerase requires the cofactor $Mn^{+2}$, $Mg^{+2}$ or $Co^{+2}$ (K. Yamanaka and N. Takahara, Agric. Biol. Chem., 41 (10) 1909 (1977). The glucose isomerase-like modified protein prepared by the present method shows no such cofactor requirement and is superior in this regard to the native enzyme. As is well known in the art, the provision of cofactors for native enzymes used in commercial process is expensive.

Many enzymes are susceptible to modeling by the present process to produce their enzyme-like modified protein analogues from selected cofactor containing native protein starting materials. Examples of such model enzymes which are subject to enzyme-like modified protein analogue production are hydrolytic enzymes, redox enzymes and transferase enzymes. By way of example: The first group, hydrolytic enzymes include proteolytic enzymes which hydrolyze proteins, e.g., papain, ficin, pepsin, trypsin, chymotrypsin, bromelin, keratinase; carbohydrases which hydrolyze carbohydrates, e.g., cellulase, amylase, maltase, pectinase, chitanase; esterases which hydrolyze esters, e.g., lipase, cholinesterase, lecithinase, alkaline and acid phosphateases; nucleases which hydrolyze nucleic acid, e.g., ribonuclease, deoxyribonuclease; and amidases which hydrolyze amines, e.g., arginase, asparaginase, histidase, and urease. The second group are redox enzymes that catalyze oxidation or reduction reactions. These include glucose oxidase, xanthine oxidase, catalase, peroxidase, lipoxidase, and cytochrome reductase. In the third group are transferase enzymes that transfer groups from one molecule to another. Examples of these are glutamicpyruvic transaminase, glutamicoxalacetic transaminase, transmethylase, phosphopyruvic transphosphorylase.

In the usual practice of the present invention, one selects a first or model enzyme, the catalytic activity of which one wishes to mimic. One then selects a second cofactor containing native protein to be modeled after the model enzyme to produce a cofactorless enzyme-like modified protein. In many cases the native cofactor containing protein is itself enzymatically active since many common cofactor containing proteins are enzymes which are available in large quantities at fairly low costs in homogeneous sample form. However, non-enzymatic cofactor containing proteins are equally useful as starting materials for use with the present process. One example of such a nonenzymatic protein which may be used as a cofactor containing native protein for the starting material is concanavalin A. Concanavalin A is available in relatively pure form at a fairly low cost from numerous commercial sources.

By practicing the process of the present invention, one can custom-tailor the cofactor containing native protein to a different stable enzyme-like modified protein form which shows the catalytic activity characteristics of the enzyme which has been modeled. The ability to custom tailor a native cofactor containing protein into a predetermined catalytic active cofactor-free protein provides advantages over available catalysts in a wide range of chemical and industrial situations. For example, if one wishes to use an enzyme which is in short supply, is very expensive or very difficult to isolate and/or purify, such an enzyme may serve as a model enzyme for the preparation of an enzyme-like modified protein analogue by the present process to mimic its activity.

A particularly advantageous feature of the present invention is the conversion of a cofactor containing native enzyme which catalyzes an undesired reaction into a modified enzyme-like protein which catalyzes a desired reaction. For example, one commercially important reaction is the following:

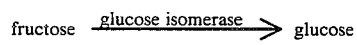

This process is interfered with when glucose oxidase is present in the glucose isomerase batch by the following reaction:

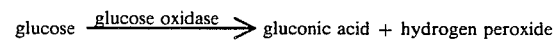

Advantageously, the present process can be used to convert native glucose oxidase, a cofactor dependent enzyme which interferes with the glucose isomerase conversion protein, into a cofactor free glucose isomerase-like modified protein. By so doing the glucose oxidase is partially denatured by removing its cofactor, namely FAD, thereby eliminating the possibility that glucose can be converted to gluconic acid. Thus by practicing the cofactor removal partial denaturation process as described herein, the process simultaneously creates a desired catalytic activity and removes, by the expedient of cofactor removal, the undesired reaction to assure that no interference with the primary reaction to form glucose occurs.

In the preferred embodiment of the invention, a native cofactor containing protein is purified and dissolved in a near neutral aqueous solvent in the presence of a suitable buffer to maintain the solution near neutrality. Subsequently, the native cofactor containing protein is partially denatured by removing the cofactor by one of the methods described above to produce, preferably a soluble form of the native protein but without the cofactor. Subsequently, an inhibitor for the model enzyme is admixed with the partially denatured cofactor free protein.

The new cofactor free partially denatured protein is stabilized by cross-linking of the protein to produce the enzyme-like modified protein. Often, cross-linking is done as disclosed above by glutaraldehyde cross-linking agent or sulphydryl rearrangement since both are relatively inexpensive to achieve. However, any of the above-described cross-linking agents can be utilized effectively in the conventional manner.

According to the present invention, the inhibitor of the model enzyme and any excess cross-linking agent are removed after synthesis of the enzyme-like cofactor free modified protein. Typically repeated dialysis or gel chromatography of the modified protein product is sufficient to remove the inhibitor.

In an alternative embodiment of the present invention, the enzyme-like modified protein produced by the preferred method outlined above is chemically immobilized on a solid support to prolong the useful life of the newly-formed enzyme-like modified protein for performing catalytic reactions.

A preferred way of carrying out the alternative embodiment of the present invention for producing a support immobilized enzyme-like modified protein comprises the steps of: partially denaturing the native holoprotein to produce the corresponding cofactor-free partially denatured apoprotein; admixing the partially denatured apoprotein with an inhibitor for the predetermined model enzyme; contacting the inhibitor-bound partially denatured apoprotein with a solid immobilization support for a time sufficient and at a temperature sufficient to produce an adsorption-immobilized apoprotein-inhibitor complex and subsequently cross-linking the support-absorbed, partially denatured apoprotein complex to form the new, immobilized enzyme-like modified protein. Any excess cross-linking agent and the inhibitor are removed from the newly formed immobilized enzyme-like modified protein to isolate the new catalytically active enzyme-like modified protein for use. Alternatively, the native holoprotein may be contacted with the solid immobilization support for a time and at a temperature sufficient to produce an adsorption immobilized holoprotein; contacting the support immobilized native holoprotein with the cofactor removal agents to produce a partially denatured apoprotein which is immobilized on the support; contacting the support immobilized apoprotein with an inhibitor for the model protein and cross-linking the inhibitor bound partially denatured apoprotein while on the immobilization support to form a new, immobilized enzyme-like modified protein. As with the previous immobilization embodiment described above, any excess cross-linking agent and the inhibitor are removed from the newly formed immobilized enzyme-like modified protein to isolate the new catalytically active enzyme-like modified protein for use.

In this embodiment of the invention, the forming enzyme-like modified protein may be immobilized on a solid support which can be inorganic or organic in composition. Particularly preferred are inorganic water-insoluble supports, such as refractory ceramic oxides, and solid organic water-insoluble supports, such as agarose-based linear cross-linked polysaccharides.

Suitable ceramic oxides include porous, particulate ceramic oxides which can be formed by compacting and sintering refractory ceramic oxide powders such as alumina powder, zirconia powder, magnesia powder, silica powder and thoria powder. Alumina powder is particularly preferred due to its chemical durability and low cost. The preparation and use of such ceramic alumina and other ceramic oxides supports is disclosed in U.S. Pat. No. 4,001,085.

Preferred immobilization supports of the solid organic water insoluble support type are agarose-based linear cross-linked polysaccharides. A particularly preferred agarose-based linear cross-linked polysaccharide is formed of alternating units of D-galactose and 3,6 anhydro-L-galactose. Such a material is available under the trade name Sepharose 4B gel. Usually such agarose-based linear cross-linked polysaccharide gels, like Sepharose 4B gel, are activated prior to immobilization of the enzyme-like modified protein thereupon by reaction of the gel with alpha-toluene sulfonyl fluoride, as exemplified hereinafter. Such preactivation increases the yield of immobilized enzyme-like modified protein during the immobilization reaction.

In another embodiment of the present invention, it has been found advantageous to immobilize the inhibitor used for the preparation of the enzyme-like modified protein. In this embodiment of the present invention, a native holoprotein is selected which is to be converted into an enzyme-like modified protein. The native holoprotein is purified and partially denatured as described above by the cofactor removal process to produce the corresponding partially denatured apoprotein. The partially denatured apoprotein is then contacted with an immobilized inhibitor, such inhibitor being immobilized on a solid support. The solid supports delineated immediately above for use with immobilization of the enzyme-like modified protein itself are suitable for the immobilization of the inhibitor also. Particularly preferred, however, is the polysaccharide formed from alternating D-galactose and 3,6 anhydro-L-galactose units, i.e., Sepharose 4B gel. After the partially denatured apoprotein is contacted with the immobilized inhibitor, the admixture is allowed to stand for a sufficient time and at a temperature suitable for the binding of the partially denatured apoprotein to the immobilized inhibitor. Subsequently, any excess unbound partially denatured apoprotein, or other protein impurity, is washed off the immobilized inhibitor support medium to isolate the immobilized inhibitor-bound partially denatured apoprotein complex. Next, the partially denatured apoprotein remaining bound to the immobilized inhibitor is cross-linked. Then, the excess cross-linking agent is washed off the immobilized inhibitor material also. The inhibitor-bound, crosslinked enzyme-like modified protein formed from the apoprotein is selectively washed off the immobilized inhibitor support to yield an enzyme-like modified protein, which shows the catalytic characteristics of the model enzyme whose inhibitor was immobilized for use in the process. As used herein, the phrase "immobilized inhibitor" means an inhibitor that is strongly attached to a solid, preferably water-soluble support, such that the inhibitor is substantially water-insoluble during all steps of the process.

In the preferred embodiment of practicing the present invention using an immobilized inhibitor for the model enzyme, the inhibitor is covalently bonded to a water-insoluble support. The support may be an organic polymeric support or inorganic support. One such organic polymeric support material is the Sepharose 4B gel indicated above. Another suitable support material is the organic water-insoluble cross-linked beaded high molecular weight polysaccharide, which has been cross-linked with epichlorohydrin, commercially available under the trade name Sephadex. Both Sephadex and Sepharose are marketed by Pharmacia of Fine Chemicals Company. Another acceptable solid support which is an organic polymeric material and water-soluble is a three-dimension polyacrylamide lattice having an interstatially disposed agarose gel, such a material is commercially available under the name Ultrogel and is marketed by LKB Produkter AB of Stockholm, Sweden.

In practicing the process of the present invention, using an immobilized inhibitor, it is preferred to use a flow-through column to practice the immobilized inhibitor methodology due to the precise control of flow-through speeds, which is available, and the ease of removal of excess reagents. The support immobilized inhibitor, which is immobilized on the supports described above by any conventional immobilization process, is wet packed into a flow-through column so that the flowing chemical reagents (the partially denatured apoprotein, the cross-linking agents and buffering agents) may be contacted with the support and the support-bound partially denatured apoprotein by simply pumping, at a controlled flow rate, various aqueous solutions of the various reagents needed through the column.

While it is preferred to use a water-insoluble support for the immobilization of the inhibitor, water-soluble supports like large proteins, such as serum albumin, may be used. In such case, the inhibitor is immobilized on the protein by conventional covalent attachment immobilization reagents, but remains in water-soluble form. Such soluble, immobilized inhibitors can be trapped in a flow-through column, as described for use, by placing ultrafiltration membranes at both ends of the column to keep the soluble inhibitor-support unit in place. The partially denatured apoprotein is then pumped through the membrane chamber, and into contact with the membrane trapped immobilized, soluble inhibitor to initiate the process. After the enzyme-like modified protein has been formed, the protein-inhibitor complex and the enzyme-like modified protein can be separated by conventional protein separation processes. For convenience of disclosure, all patent documents and publications disclosed hereinabove are incorporated by reference.

EXAMPLE 1

PART A

Partial Denaturation of Concanavalin A by Production of Apo Concanavalin A

Fifty mg of concanavalin A (hereinafter Con A) protein purchased from ICN Nutritional Biochemicals, Inc., Catalog No. 101410, Lot 1981, is dissolved in 100 ml of distilled deionized water and brought to pH 3.0 by the slow addition of 17M acetic acid. The solution is stirred at room temperature for one hour and dialyzed against a solution of acetic acid, pH 3.0, at 5° C., for 24 hours, with two dialysate changes. The above process removes the cofactor, namely, $Ca^{+2}$ and $Mn^{+2}$ metal ion, from the Con A protein to produce a cofactor free partially denatured protein. Such a cofactor removal by demetallization is reported by J. W. Becker et al. in *Nature*, 259, 406–409 (1976).

PART B

Addition of Inhibitor

The above solution of the demetalized cofactor free partially denatured Con A is contacted with an inhibitor for glucose isomerase as follows. A two percent solution of D-mannitol inhibitor for glucose isomerase, purchased from Sigma Chemicals Co., Catalog No. M-4125, Lot 81 F-0517, is prepared in distilled deionized water. Two ml of the inhibitor solution is added to the demetallized partially denatured Con A solution above in a dropwise fashion. The solution containing the partially denatured cofactor free Con A and the D-mannitol inhibitor is stirred at room temperature for two hours.

PART C

Cross-linking

Next to the above solution is added 400 microliters of eight percent glutaraldehyde cross-linking reagent, purchased from Polyscience Corporation, Catalog No. 0216. The solution now containing the cofactor free, partially denatured Con A, the inhibitor and the cross-linking agent is stirred at 5° C. for six hours. The solution is then dialyzed against 0.01M sodium acetate buffer at pH 6.0. The dialysis is continued for 48 hours with six changes of dialysate. The material in the dialysis bag is then lyophilized and stored at −60° C. until assayed for glucose isomerase activity.

A reference preparation is made by cross-linking the demetallized cofactor free partially denatured Con A as described above without any prior reaction with the D-mannitol inhibitor.

PART D

Results

The assay for glucose isomerase activity in the glucose isomerase-like modified protein is conducted as follows. The glucose isomerase-like modified protein is assayed for glucose isomerase activity using reference grade beta-D-fructose material from Pfanstiel Laboratories, Catalog No. RFG 100, Lot 14166. The glucose formed by the glucose isomerase-like modified protein is measured by the glucose oxidase-peroxidase procedure as disclosed by A. S. Kesden in Abstracts of the 129th Meeting of the ACS, page 31C (1956). The assay method is based upon the following reactions. The glucose isomerase-like modified protein produced according to the present invention catalyzes the isomerization of fructose to glucose. The glucose oxidase enzyme oxidizes the glucose to produce glucono lactone and hydrogen peroxide, in the presence of molecular oxygen. The hydrogen peroxide thereby produced is acted upon by the peroxidase enzyme to transfer molecular oxygen to the dye ortho-dianisidine to produce the oxidized dye which is brown in color. The oxidized ortho-dianisidine has an absorption maxima between 425–475 millimicrons and such absorption is proportional to the glucose concentration present in the reaction mixture. A glucose standard curve is obtained by the following procedure.

Preweighed capsules containing 500 units of glucose oxidase, 100 units of peroxidase and a buffer salt are purchased from Sigma Chemical Company as PGO-enzyme, Stock No. 510-6. Each capsule of PGO-enzyme material is dissolved in 100 ml of distilled deonized water by gentle shaking and stored in an amber colored flask until needed. The ortho-dianisidine hydrochloride is purchased from Sigma Chemical Company as Stock No. 510-50 in preweighed vials containing 50 mg each of the ortho-dianisidine. Each vial is reconstituted in 20 ml of distilled deionized water.

The PGO-enzyme-color reagent solution is prepared by mixing 100 ml of the PGO solution as described above with 1.5 ml of the color reagent described above and shaking gently until complete admixture has occurred.

A standard curve for glucose is constructed by the following procedure.

A standard glucose solution, purchased from Sigma Chemical Company as stock solution 635-100 containing 5.56 millimoles per liter of glucose is diluted one to 100 with distilled deionized water. The thus prepared solution contains 0.0556 micromoles of glucose per ml of solution. Aliquots of 50, 100, 150 and 200 microliters of the above diluted glucose standard solution are placed in test tubes and the volumes equalized to 200 microliters by the addition of appropriate volumes of distilled deionized water. To each tube is added two ml of the PGO-chromogen mixture. A blank consisting of 200 microliters of distilled deionized water, totally devoid of glucose, is also prepared and two ml of PGO-chromogen is added to this solution. The contents of the tubes are mixed in a vortex-type mixture and incubated for 30 minutes at 37° C. The absorbance reading is taken at 450 millimicrons for the blank and the glucose standards using a Cary Model 15 recording spectrophometer set on a 0.1 scale total absorbance using distilled deionized water in the reference cell. The absorbance of the blank is subtracted from the values for the 91ucose standards and a standard curve is plotted with micromoles of glucose vs. optical density of the solution.

To assay for glucose isomerase activity in the glucose isomerase-like modified protein and cross-linked apo Con A reference, approximately one mg of lyophilized modified protein is dissolved in two ml of 0.05M sodium phosphate buffer at pH 6.0. The absorbance at 280 millimicrons of this solution is 0.98. Using the standard absorbance value for a one percent solution of Con A as 12.4 as disclosed by D. M. Kirschenbaum in *Int. J. Protein Res.*, 4, 63 (1972) the protein concentration of the solution is calculated to be 800 micrograms per milliliter.

A substrate solution for the glucose isomerase-like modified protein activity assay is prepared by dissolving 36 mg of reference grade fructose substrate in 10 ml of 0.05M phosphate buffer, pH 6.0.

The sample and control assays are set up in the following fashion. The sample assay is conducted using 100 microliters of substrate solution admixed with 100 microliters of modified protein solution from above containing 80 micrograms of protein in a test tube. The mixture is incubated at room temperature for a period of time and the glucose produced is determined by the PGO method described above. Separate incubation mixtures are set up for varying reaction periods and glucose production is measured as described above.

For the control assay, the modified Con A solution and the fructose are incubated in separate tubes and 100 microliters of each is mixed together and at the end of a definite reaction period. A control is performed for each sample assay and the glucose content is measured as it is done for the sample above.

The difference in the optical densities at 450 millimicrons, between the sample and the blank for the control is computed, and the glucose produced due to the glucose isomerase-like modified protein activity is obtained from the standard glucose curve prepared above. The units of glucose isomerase activity value is calculated by regression analysis and expressed as micromoles of glucose produced per minute per gram of protein.

The assay results were as follows:

| | Substrate Fructose (Activity in Units/gm ± standard deviation) |
|---|---|
| Native Con A - no inhibitor no cross-linking | −0.2 ± 0.04 |
| Apo Con A - no cross-linking | −0.01 ± 0.03 |
| Native Con A - inhibitor contacted, cross-linked but not partially denatured | −0.5 ± 0.1 |
| Enzyme-like modified protein according to the invention | 1.8 ± 0.4 |

The above results demonstrate that the glucose isomerase-like modified protein produced according to the present invention exhibits enzymatic activity with respect to fructose substrate for glucose isomerase. No such activity is previously detected in the native Con A. This illustrates the conversion of one genus of protein, namely, a non-enzymatic Con A starting material, to another genus of protein, namely, an enzymatically active glucose isomerase-like modified protein of the isomerase enzyme group.

Following control experiments are done with concanavalin A:

1. To confirm that the native Con A used for modification does not possess any glucose isomerase activity, a solution of Con A (ICN Nutritional Biochem., Cat. No. 101410, Lot 1981) is prepared by dissolving 20 mg in 10 ml. of distilled, deionized water, and dialyzed overnight against 0.01 M sodium acetate buffer pH 5.0. This dialyzed solution of native Con A is assayed for glucose isomerase activity, as described in Example 4.

2. To confirm that no glucose isomerase activity is generated if native Con A is modified without the partial denaturation step, which is done by removing the metal ions, the following experiment is done. Fifty mg. of Con A from the same source and lot used for the modification preparations is dissolved in 100 ml. of distilled deionized water, and the pH of the solution is adjusted to 3.0. Immediately after the adjustment of pH, 2 ml of a 2% solution of D-mannitol inhibitor is added and the pH of the solution is adjusted to 7.0 with 0.1N NaOH. This solution of Con A containing the mannitol inhibitor is stirred at room temperature for two hours, cooled to 5° C., and then 400 microliters of glutaraldehyde cross-linking reagent is added. The cross-linking is done for six hours at this temperature, and the cross-linked solution is dialyzed against distilled water for 48 hours, with five changes of the dialysate. The dialyzed solution is lyophilized and assayed for glucose isomerase activity as described in Example 4.

No glucose isomerase activity is detected in the above two reference preparations.

EXAMPLE 2

PART A

Partial Denaturation of Glucose Oxidase by Production of Apo Glucose Oxidase

Glucose oxidase is a flavin containing glycoprotein which catalyzes the oxidation of glucose to gluconic acid. The glycoprotein contains two moles of flavin-adenine dinucleotide (FAD) per mole of enzyme, and has a molecular weight of 160,000 consisting of two identical subunits. The apoenzyme of glucose oxidase prepared by the acid-ammonium sulfate method has the same molecular weight as the holoenzyme. This is reported in an article by: Swoboda, B. E. P., *Biochem. Biophys. Acta*, 175, 365–379, (1969). He also showed that apoenzyme prepared by the acid-ammonium sulfate method has no glucose oxidase catalytic activity, but that incubating the apoenzyme with an excess of FAD the holoenzyme activity is regenerated. According to the same article: p. 365–379, "It has been proposed that the apoenzyme exists in two forms, $P_1$ and $P_2$, which are probably in equilibrium with one another. The $P_1$ (80%) has a loose flexible foil structure and a molar frictional ratio of 2.2 at pH 5.6. The $P_2$ form (20%) has a more compact structure and a frictional ratio of 1.2." Thus, the structure of glucose oxidase is partially denatured by removal of the FAD portion of the enzyme.

The apoenzyme of glucose oxidase is prepared by removing the FAD of glucose oxidase using the method as described in the article: Tsuge, H. and Mitsuda, H., *The Journal of Vitaminology* 17, 24–31, (1971).

About 100 mg of glucose oxidase (type VII) from *Aspergillus niger*, purchased from Sigma Chemical Company, No. G-2133, Lot 88C-0064, is dissolved in 20 milliliters of 0.01 M sodium acetate buffer, pH 5.5 and ammonium sulfate granules are added slowly to bring the solution to 80% saturation. The glucose oxidase solution is kept at 0° C. during the course of this procedure. The pH of the solution is adjusted to 2.0 with 4 N HCl and allowed to stand for 30 minutes. The resulting precipitate is centrifuged at 27,000 g. for 30 minutes. The yellow supernatant is decanted and the slightly yellowish precipitate is dissolved in 2.5 milliliters of 2.0 M ammonium acetate. The resulting solution is added dropwise to 25 milliliters of acidic-85% saturated ammonium sulfate solution (pH 2.0 adjusted with 4 N HCl). Using the resulting precipitate, the above treatment is repeated two times so that the supernatant fraction appears colorless.

The precipitate is dissolved in 30 ml of 0.05 M sodium phosphate buffer, pH 7.0 and dialyzed against 0.001 M tris-HCl buffer, pH 7.0 for 17 hours using a dialysis tubing having a molecular weight cut-off of 12–14,000 daltons. The concentration of the dialyzed apoenzyme is determined in accordance with the teachings of D. M. Kirschenbaum in *Analytical Biochemistry* 82, pages 83–100, 1977. The absorbance at 280 nm is measured as 1.96. Using the absorbance coefficient value of 10.6, the concentration of the solution is about 1.84 milligrams per milliliter.

The activity of the native glucose oxidase and the apoenzyme is determined by the colorimetric determination of hydrogen peroxide produced during the coupled reaction with 0-dianisidine and peroxidase. This assay procedure is obtained from the *Worthington Enzyme Manual*, pages 19–20, 1972. The activity is expressed as units/milligram where one unit of glucose oxidase activity is that amount of enzyme liberating one micromole of $H_2O_2$ per minute at 25° C. The results of this assay shows that the apoenzyme has only 0.09% of the initial activity of the native glucose oxidase. This trace of activity is subsequently removed to give pure activity-free apoenzyme.

PART B

Preparation of Immobilized Model Enzyme Inhibitor

A method of purifying this apoenzyme, that is, a method of removing all the native glucose oxidase activity, is developed in which the dialyzed apoenzyme of PART A is added to a cellobiose inhibitor gel affinity column.

A glass walled chromatography column of about 5.0 cm length and about 1.5 cm interior diameter is used in the procedure. The immobilized glucose isomerase inhibitor, namely cellobiose, gel is prepared as follows. The inhibitor, cellobiose, is immobilized on a solid, organic, water insoluble support comprising an agarose based, linear, cross-linked polysaccharide having alternating residues of D-galactose and 3,6 anhydro-L-galactose. The immobilization support is available from Pharmacia Fine Chemicals under the name Sepharose 4B Gel.

The column material is prepared in accordance with the process outlined by Sundberg and Porath in *J. of Chromatography* entitled "Preparation of Adsorbents for Biospecific Affinity Chromatography", 90, pg. 87–98 (1974). The procedure is as follows:

Twenty-five grams of Sepharose 4B Gel is washed on a glass filter-funnel with two liters of distilled deionized water and suction-dried for five minutes under vacuum. To the suction-dried gel is added 25 milliliters of 1,4 butanediol diglycidyl ether and 25 milliliters of 0.6 M NaOH containing two milligrams of sodium borohydride per milliliter of solution. The resulting suspension is shaken for five hours on an Eberbach shaker at low speed.

After five hours, the suspension is washed on a glass filter-funnel with 750 milliliters of distilled, deionized water; then 750 milliliters of 0.02 M sodium phosphate buffer, pH 7.5; 750 milliliters of 0.001 M tris-HCl buffer, pH 7.0; 750 milliliters of 0.02 M glycine-HCl buffer, pH 3.0 and finally 750 milliliters of 0.05 M sodium carbonate buffer, pH 10.0 and suction-dried for five minutes.

To the suction-dried gel is added 25 milliliters of a 2% D(+) cellobiose solution. The cellobiose solution is made from 500 mg of cellobiose in 25 milliliters of 0.05 M sodium carbonate buffer, pH 10 with the cellobiose from Sigma Chemical Co., No. C-7252, lot No. 110F-0656. The cellobiose-gel solution is shaken at slow speed for 16 hours.

After 16 hours, the suspension is washed on a glass filter-funnel with 750 milliliters of 0.05 M sodium carbonate buffer, pH 10.0; 750 milliliters of distilled deionized water; 750 milliliters of 0.001 M tris-HCl buffer, pH 7.0; 750 milliliters of 0.02 M glycine-HCl, pH 3.0 and finlly 750 milliliters of 0.05 M sodium carbonate buffer, pH 9.5. The gel is suction-dried under vacuum for five minutes.

Twelve and one-half grams of the suction-dried material is added to 20 milliliters of 2.0 M ethanolamine solution. The ethanolamine reagent is made by adding 2.54 milliliters of 95% ethanolamine to sufficient 0.05 M sodium carbonate buffer, pH 9.5, to make 20 milliliters volume. The gel-ethanolamine solution is shaken for five hours and then washed on a glass filter-funnel as follows, in the order given, 500 milliliters of 0.05 M sodium carbonate buffer, pH 9.5; 500 milliliters of 0.02 M sodium phosphate buffer, pH 7.5; 500 milliliters of 0.001 M tris-HCl buffer, pH 7.0 and 500 milliliters of distilled deionized water. The gel is next suction-dried under vacuum, resuspended in distilled deionized water and stored under refrigeration until the column is packed.

To prepare the column for acceptance of the dialyzed apoenzyme, the column is packed about 3.8 centimeters high with immobilized cellobiose-inhibitor gel. After packing the column, it is purged of possible contaminants by washing the column as follows: 200 ml of 0.001 M tris-HCl buffer, pH 8.0; 200 ml of 0.05 M sodium acetate buffer, pH 5.5; 150 ml of 2.0 M guanidine HCl aqueous solution; and finally with 200 ml of 0.1 M sodium phosphate buffer, pH 7.0.

PART C

Purification of Dialyzed Apoenzyme of Glucose Oxidase

The column of PART B is purged with a flowing stream of 0.1 M sodium phosphate buffer, pH 7.0, flowing at 1.5 ml per minute. Ten ml of dialyzed apoenzyme of PART A is injected at the head of the column. The eluant from the column is monitored at 254 nm. When that portion of the apoenzyme not binding to the immobilized cellobiose inhibitor eluted from the column, it is collected and determined to contain 16.2 mg of apoenzyme by using the method of D. M. Kirschenbaum described above. Accordingly, about 2.3 milligrams of apoenzyme is bound to the inhibitor on one exposure to the column.

A portion of the apoenzyme not binding to the cellobiose gel is assayed for glucose oxidase activity by the colorimetric determination of hydrogen peroxide produced during the coupled reaction of ortho-dianisidine and peroxidase described above. All of the glucose oxidase activity (expressed as total units) in the ten milliliter sample of dialyzed apoenzyme added to the column is present in the portion of the apoenzyme not binding to the column. Therefore, the apoenzyme still bound to the column has no glucose oxidase activity and has been purified by the affinity chromatography procedure.

PART D

Cross-linking

The 2.3 milligrams of inhibitor column bound apoenzyme which is devoid of any native glucose oxidase activity is cross-linked with dimethyl suberimidate dihydrochloride purchased from Sigma Chemical Company, No. 7636, Lot 31F-0225. The cross-linking agent is prepared by dissolving 0.1 gram of dimethyl suberimidate dihydrochloride in 25 ml of 0.1 M sodium phosphate buffer, pH 7.0. The outlet of the column of PART C is connected to the top of the column to form a closed recirculation flow loop. The 25 ml of cross-linking agent is recirculated through the column for about 90 minutes at a flow rate of 1.5 ml per minute.

PART E

Collection of the Enzyme-Like Modified Protein

The recirculating system of PART D is disconnected and a 0.1 M sodium phosphate buffer, pH 7.0, is pumped through the column now containing the inhibitor-bound, cross-linked and thereby stabilized enzyme-like modified protein, at 1.5 ml per minute. Approximately two bed volumes (15 ml) of the pH 8.0 sodium phosphate buffer is pumped through the column to remove any excess dimethyl suberimidate dihydrochloride. Then a 0.05 M glycine-HCl buffer, pH 3.0 is pumped through the column at 1.5 ml per minute. After about 20 minutes, no modified protein had eluted from the column. The eluant is changed to 0.05 M glycine-NaOH buffer, pH 9.0. After about 5 minutes, modified protein began eluting from the column. About 7 ml of eluant is collected before the modified protein stopped eluting.

The absorbance at 280 nm is determined to be 0.041, thus, about 0.27 mg of modified protein is found to be collected The eluant is changed to 0.05 M glycine-NaOH buffer, pH 9.5. After pumping this pH 9.5 glycine-NaOH buffer through the column at a flow rate of 1.5 ml per minute for five minutes, additional modified protein eluted from the column. About 12 ml of eluant is collected before the modified protein stopped eluting. The absorbance at 280 nm is determined as in PART A to be 0.112, thus about 1.3 milligrams of modified protein is found to be collected.

PART F

Results I

The following activity with respect to fructose substrate for glucose isomerase is recorded from a sample of the glucose isomerase-like modified protein prepared according to the invention in PARTS A-E above.

A portion of the eluant collected in PART E is analyzed for glucose isomerase enzymatic activity as follows: The activity is determined colorimetrically using a Sigma Chemical Company Glucose Diagnostic Kit No. 510-A by measuring the amount of glucose generated from fructose as a function of time.

The procedure is based on the coupled enzymatic reactions of glucose oxidase and peroxidase with ortho-dianisidine as a chromogen. The intensity of the brown color measured at 450 nm is proportional to the glucose concentration.

The reaction solution is prepared as follows: 2.0 ml of glucose isomerase-like modified protein of PART E, collected at pH 9.5, and 2.0 ml of 0.1 M beta-D fructose substrate for glucose isomerase in 0.05 M sodium acetate buffer, pH 5.5 are admixed.

The control solution No. 1 is prepared by mixing 2.0 ml of glucose isomerase-like modified protein of PART E, collected at pH 9.5 with 2.0 ml of 0.05 M sodium acetate buffer, pH 5.5.

The control solution No. 2 is prepared by mixing 2.0 ml of 0.05 M glycine-NaOH buffer, pH 9.5 with 2.0 ml of 0.1 M beta-D fructose substrate in 0.05 M sodium acetate buffer, pH 5.5.

The final pH of both controls and the reaction solution is 8.5.

The reaction solution, control No. 1 and control No. 2 are placed in a 37° C. water bath and gently shaken. After incubating at 37° C. for 10 minutes, 20 minutes, 30 minutes and 60 minutes; 0.5 ml of each solution is removed and added to 1.0 ml of a solution containing glucose oxidase, peroxidase and ortho-dianisidine (PGO). The PGO reaction is allowed to proceed to completion for approximately 30 minutes at 37° C., and then the absorbance at 450 nm is measured on a Cary 14 spectrophotometer.

For each time interval, the change in absorbance is calculated by subtracting the absorbance of control No. 1 and control No. 2 from the absorbance of the reaction solution and then adding the absorbance of 1.0 ml of PGO solution added to 0.25 ml of 0.05 M glycine-NaOH buffer, pH 9.5 and 0.25 ml of 0.05 M sodium acetate buffer, pH 5.5, i.e. Reaction solution−control No. 1−control No. 2+PGO and buffer=change in absorbance.

Then using the calculated change in absorbance for each time interval listed above, a linear regression analysis is performed. The resulting slope (change in absorbance per min.) is used in the following equation to calculate the activity in units per gram glucose isomerase-like modified protein.

$$\text{Units/g} = \frac{(\text{change } A/\text{min.}) (SV) (k)}{(MP)}$$

Wherein: MP is grams of enzyme-like modified protein in the reaction mixture; k is 0.343 micromoles per milliliter-absorbance, the constant calculated from a plot of known glucose standards versus the change in absorbance as determined by the Sigma Glucose Diagnostic Kit No. 510-A;

change $A$/min. is the change in absorbance per minute; and

SV is sample volume in milliliters.

The modified protein eluted at pH 9.0 had no detectable glucose isomerase activity.

The calculated activity from the 37° C. assay results for the glucose isomerase-like modified protein eluted at pH 9.5 is as follows:

|  | SUBSTRATE Fructose (Activity in Units/gram) |
| --- | --- |
| Apo glucose oxidase | 0.0 |
| Enzyme-like modified protein | 2.7 ± 0.2 |

The results show that the glucose isomerase-like modified protein of PART E exhibits catalytic activity with respect to glucose isomerase substrate, fructose, where no glucose isomerase activity is previously detected in the apo glucose oxidase starting material.

The quantity of glucose isomerase-like modified protein used in this assay is $1.32 \times 10^{-3}$ micromoles. The molecular weight used to calculate micromoles is 160,000 daltons.

From the calculated activity above, there is $3.4 \times 10^{-2}$ micromoles of fructose converted to glucose in 60 minutes.

Therefore, approximately 2.6 micromoles of fructose substrate is converted to glucose per micromole of glucose isomerase-like modified protein during the assay.

This identifies the above reaction as a catalytic process due to the measured turnover rate disclosed above.

This Example illustrates the conversion of glucose oxidase, an enzyme of the oxido-reductase group, to a glucose isomerase-like modified protein. Glucose isomerase is a member of the isomerase group of enzymes.

Results II

Assay of Dialyzed Modified Glucose Isomerase-Like Protein

A portion of the glucose isomerase-like modified protein eluted at pH 9.5 is dialyzed against 0.02 M sodium phosphate buffer, pH 8.0, for 17 hours using a dialysis tubing having a molecular weight cut-off of 12–14,000 daltons. The concentration of the dialyzed glucose isomerase-like modified protein is determined by using the method of D. M. Kirschenbaum described in PART A. The absorbance at 280 nm is measured as 0.06. Using the absorbance coefficient value of 10.6, the concentration of the solution is 0.057 mg per ml.

The following activity with respect to fructose substrate for glucose isomerase is recorded from a sample of dialyzed glucose isomerase-like modified protein prepared according to the invention in PARTS A–E.

A portion of the dialyzed modified protein is analyzed for glucose isomerase enzymatic activity as follows: The activity is determined colorimetrically using the Sigma Glucose Diagnostic Kit No. 510-A described in PART F Result I.

The reaction solution is prepared as follows: 2.0 ml of dialyzed modified protein of PART E, collected at pH 9.5, and 2.0 ml of 0.1 M beta-D fructose dissolved in distilled deionized water.

The control solution No. 1 is prepared by mixing 2.0 ml of dialyzed modified protein of PART E, collected at pH 9.5 with 2.0 ml of distilled deionized water.

The control solution No. 2 is prepared by mixing 2.0 ml of 0.02 M sodium phosphate buffer, pH 8.0 with 0.1 M beta-D fructose in distilled deionized water.

The final pH of both controls and the reaction solution is 8.0.

The reaction solution, control No. 1 and control No. 2 are placed in a 37° C. water bath and allowed to gently shake. After incubating at 37° C. for 5 minutes, 10 minutes, 30 minutes, 45 minutes and 60 minutes; 0.5 ml of each solution is removed and added to 1.0 ml of a solution containing glucose oxidase, peroxidase and orthodianisidine (PGO). The PGO reaction is allowed to proceed to completion in approximately 30 minutes at 37° C., and then the absorbance at 450 nm is measured on the Cary 14 spectrophotometer.

For each time interval, the change in absorbance is calculated by subtracting the absorbance of control No. 1 and control No. 2 from the absorbance of the reaction solution and then adding the absorbance of 1.0 ml of PGO solution added to 0.5 ml of 0.02 M sodium phosphate buffer, pH 8.0, i.e. Reaction solution−control No. 1−control No. 2+PGO & buffer=change in Abs.

Then using the calculated change in absorbance (Abs.) for each time interval listed above, a linear regression analysis is performed. The resulting slope (change in Abs./min.) is used in the equation described in Results I above to calculate the activity in units per gram modified protein.

The calculated activity from the 37° C. assay results for the dialyzed modified protein eluted at pH 9.5 is as follows:

|  | SUBSTRATE Fructose (Activity in Units/gram) |
| --- | --- |
| Apo glucose oxidase | 0.0 |
| Enzyme-like modified protein | 3.9 ± 0.7 |

Figure 2:
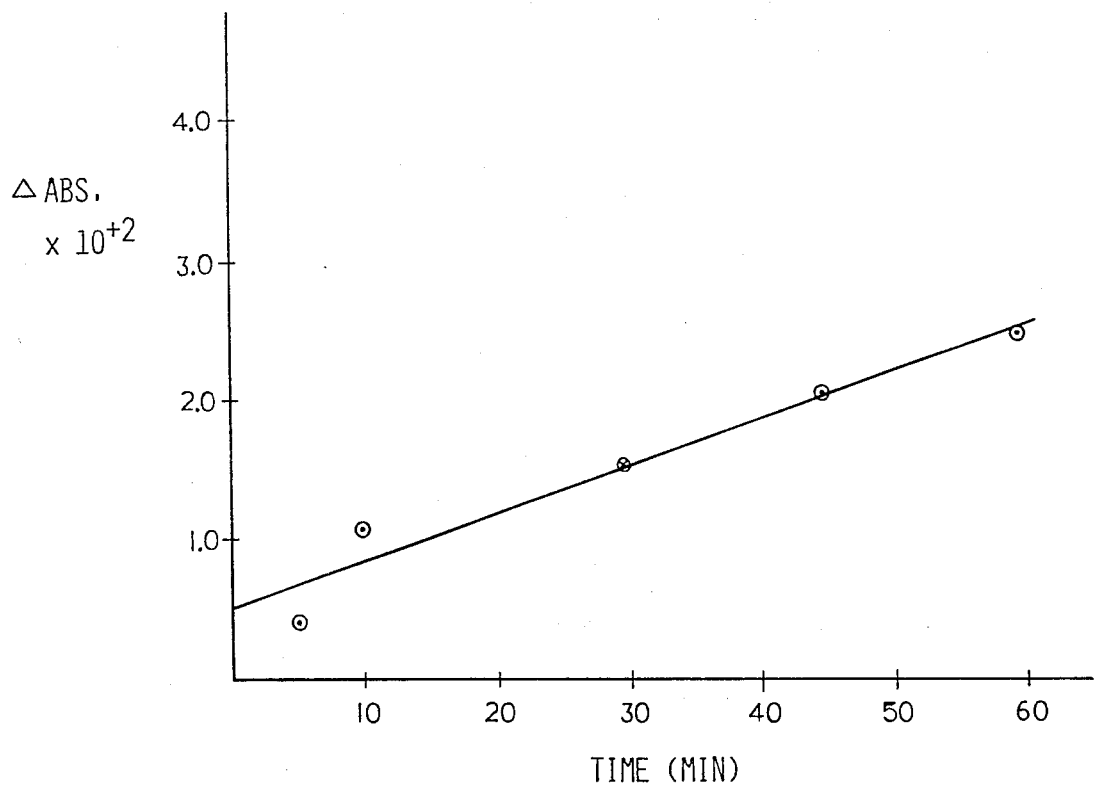
FIG. 2 illustrates the catalytic activity of the dialyzed enzyme-like modified protein prepared in Example 2.

The quantity of dialyzed glucose isomerase-like modified protein used in this assay is $7.13 \times 10^{-4}$ micromoles. From the calculated activity, there is $2.74 \times 10^{-2}$ micromoles of fructose converted to glucose in 60 minutes. The activity data measured above is illustrated graphically at FIG. 2 and shows the linearity of the catalytic activity as a function of time. Therefore, approximately 37 micromoles of fructose substrate is converted or turned over to glucose per micromole of glucose isomerase-like modified protein during this assay.

This identifies the above reaction as a catalytic process.

Results III

Immobilization of Dialyzed Glucose Isomerase-Like Modified Protein

A portion of the glucose isomerase-like modified protein collected in PART E, collected at pH 9.5 is dialyzed as described above and immobilized onto an activated Speharose-4B gel support.

Sepharose-4B is activated using alpha-toluene sulfonyl fluoride by the method of Bulow and Mosbach reported in *Biochemical and Biophysical Research Communications*, Vol. 107, pp. 458–464 (1982).

One hundred and eight grams of Sepharose-4B Gel (from Pharmacia Lot 23332) is filtered on No. 2 Whatman paper and washed with 1500 ml of distilled water. The gel is then transferred to a 2 liter flask and 100 ml of water added, followed by 50 ml portion of acetone at 2–3 minute intervals until the total volume of the mixture is 800 ml. The flask is swirled during this operation to insure mixing. The final mixture of gel and acetone sat one hour before being used.

The gel/acetone mixture is then filtered on Whatman No. 2 paper and washed with 2 liters of acetone followed by 1500 ml of anhydrous acetone. Anhydrous acetone is obtained by distilling acetone from molecular sieves, type 4A.

The anhydrous gel is then placed in a 1 liter flask and 100 ml of anhydrous acetone (from Matheson, Coleman and Bell, Lot SX299 2781) is added, followed by 4.1 ml of triethylamine (Fisher Chem. Co., Lot 720990). Mixture is stirred rapidly while 1.88 grams of alpha-toluene sulfonyl fluoride (from Sigma Chemical Co., Lot 126C-0412) is added in small portions over a two minute period. The mixture is stirred another 20 minutes and then filtered on No. 2 Whatman paper and washed with 2 liters of acetone.

The activated gel is then placed in a 2 liter flask and 100 ml of acetone added followed by 50 ml portions of 0.001 M HCl at 2–3 minute intervals, until the total volume of the mixture is 700 ml, then a 300 ml portion is added. The mixture is swirled during the operation. The gel is then filtered on Whatman No. 2 filter paper and washed with 2 liters of 0.001 M HCl. The resulting activated gel is stored at 5° C. until used.

Four grams of this activated Sepharose-4B gel is washed with approximately 500 ml of 0.1 M sodium phosphate buffer, pH 7.5. The washed activated gel is centrifuged at 12,100 g. per minute for 15 minutes and the supernatant decanted. Then 2.0 grams of this washed activated Sepharose-4B gel is weighed out and 4.5 ml of dialyzed glucose isomerase-like modified protein is added to the gel, which equals 0.26 milligrams of modified protein. The slurry is placed in a 5° C. cold water bath and allowed to gently shake. After incubating at 5° C. for 18 hours, the suspended gel-protein solution is centrifuged at 10,000 revolutions per minute for 10 minutes. The supernatant is poured off and the volume is found to be 4.6 ml. The protein concentration of the supernatant is determined by using the method of D. M. Kirschenbaum described in PART A. The absorbance at 280 nm is measured at 0.03. Using the absorbance coefficient of 10.6, the concentration of the supernatant is 0.028 mg per ml, thus about 0.13 mg of modified protein is immobilized onto 2.0 grams of the activated Sepharose-4B gel.

Before assaying the immobilized glucose isomerase-like modified protein for activity the gel is suspended in 0.1 M sodium phosphate buffer, pH 8.0 and centrifuged at 1085 g. for five minutes. The supernatant is poured off and the immobilized glucose isomerase-like modified protein is separated into two 1.0 gram samples.

The following activity with respect to fructose substrate for a glucose isomerase is recorded from the 1.0 gram sample of immobilized glucose isomerase-like modified protein as prepared above.

A 1.0 gram portion of the immobilized modified protein is analyzed for glucose isomerase enzymatic activity as follows: The activity is determined colorimetrically using the Sigma Glucose Diagnostic Kit No. 510-A described in PART F above.

The reaction solution is prepared as follows: 2.0 ml of 0.1 M sodium phosphate buffer, pH 8.0 is added to 1.0 ml of 0.2 M beta-D fructose dissolved in deionized water and this is added to 1.0 gram of swelled immobilized glucose isomerase-like modified protein gel.

The control solution No. 1 is prepared by adding 2.0 ml of 0.1 M sodium phosphate buffer, pH 8.0 and 1.0 ml of distilled deionized water to 1.0 gram of swelled immobilized glucose isomerase-like modified protein gel.

The control solution No. 2 is prepared by adding 2.0 ml of 0.1 M sodium phosphate buffer, pH 8.0 and 1.0 ml of 0.2 M beta-D fructose dissolved in distilled deionized water to 1.0 gram of swelled activated Sepharose-4B gel used in the immobilization procedure above.

The final pH of the two controls and the reaction solution is 8.0.

The reaction solution, control No. 1 and control No. 2 are placed in a 37° C. water bath and allowed to gently shake. After incubating at 37° C. for 30 minutes, 120 minutes and 180 minutes; each solution is centrifuged at 1085 g. for six minutes and 0.5 ml of the supernatant of each solution is added to 1.0 ml of a solution containing glucose oxidase, peroxidase, and O-dianisidine (PGO). The PGO reaction is allowed to proceed to completion in approximately 30 minutes at 37° C., and then the absorbance at 450 nm is measured on a Cary 14 spectrophotometer.

For each time interval, the change in absorbance is calculated by subtracting the absorbance of control No. 1 and control No. 2 from the absorbance of the reaction solution and then adding the absorbance of 1.0 ml of PGO solution added to b 0.1 M sodium phosphate buffer, pH 8.0, i.e., Recation solution−control No. 1−control No. 2+PGO & buffer=change in Abs.

Then using the calculated change in Abs. for each time interval listed above, a linear regression analysis is performed. The resulting slope (change in Abs./min.) is used in the equation described in Results I above substituting for grams of modified protein the grams of immobilized modified protein gel to calculate the activity in units per gram swelled immobilized glucose isomerase-like protein gel.

The calculated activity for the pH 8 material from the 37° C. assay results for the immobilized glucose isomerase-like protein is as follows:

|  | SUBSTRATE Fructose (Activity in Units/gram swelled gel) |
|---|---|
| Immobilized Enzyme-like modified protein | $1.5 \pm 0.1 \times 10^{-3}$ |

Approximately 0.0637 mg of glucose isomerase-like modified protein is determined to be bound to each gram of swelled activated Sepharose-4B gel (see Results III above).

The quantity of modified glucose isomerase-like protein used in this assay is $4.0 \times 10^{-4}$ micromoles. From the calculated activity above, there is $2.77 \times 10^{-1}$ micromoles of fructose converted to glucose in 180 minutes.

Therefore, approximately 696 micromoles of fructose is converted or turned over to glucose per micromole of glucose isomerase-like modified protein during the assay per micromole of modified protein.

This identifies the above reaction as a catalytic process.

After completing the assay of swelled immobilized modified protein gel at pH 8.0, the gel is washed with approximately 200 ml of 0.1 M sodium phosphate buffer, pH 7.5 and stored at 5° C. for 17 hours overnight.

The gel is washed three more times with 0.1 M sodium phosphate buffer, pH 7.0 and the following solutions prepared for assaying the immobilized modified protein gel for glucose isomerase enzymatic activity at pH 7.0.

The reaction solution is prepared as follows: 2.0 ml of 0.1 M sodium phosphate buffer, pH 7.0 is added to 1.0 ml of 0.2 M beta-D fructose dissolved in distilled deionized water and this is added to 1.0 gram of swelled immobilized glucose isomerase-like modified protein gel.

The control solution No. 1 is prepared by adding 2.0 ml of 0.1 M sodium phosphate buffer, pH 7.0 and 1.0 ml of distilled deionized water to 1.0 gram of swelled immobilized glucose isomerase-like modified protein gel.

The control solution No. 2 is prepared by adding 2.0 ml of 0.1 M sodium phosphate buffer, pH 7.0 and 1.0 ml of 0.2 M beta-D fructose dissolved in distilled deionized water to 1.0 gram of swelled activated Sepharose-4B gel used in the immobilization procedure above.

The final pH of the two controls and the reaction solution is 7.0.

The reaction solution, control No. 1 and control No. 2 are placed in a 37° C. water bath and allowed to gently shake. After incubating at 37° C. for 30 minutes, 180 minutes and 240 minutes; each solution is centrifuged at 1085 g. for six minutes and 0.5 ml of the supernatant of each solution is added to 1.0 ml of a solution containing glucose oxidase, peroxidase and O-dianisidine (PGO). The PGO reaction is allowed to proceed to completion in approximately 30 minutes at 37° C., and then the absorbance at 450 nm is measured on a Cary 14 spectrophotometer.

For each time interval, the change in absorbance is calculated by subtracting the absorbance of control No. 1 and control No. 2 from the absorbance of the reaction solution and adding the absorbance of 1.0 ml of PGO solution added to 0.1 M sodium phosphate buffer, pH 7.0, i.e., Reaction solution−control No. 1−control No. 2+PGO & buffer=change in Abs.

Then using the calculated change in Abs. for each time interval listed above, a linear regression analysis is performed. The resulting slope (change in Abs./min.) is used in the equation described in Results I, above substituting for grams of modified protein the grams of immobilized modified protein gel to calculate the activity in units per gram swelled immobilized glucose isomerase-like protein gel.

The calculated activity for the immobilized glucose isomerase-like protein stored overnight at pH 7.0 and assayed at 37° C. is as follows:

| | SUBSTRATE Fructose (Activity Units/gram swelled gel) |
|---|---|
| Immobilized Enzyme-like Modified Protein | $2.1 \pm 0.3 \times 10^{-4}$ |

The activity data measured above is illustrated graphically as part of FIG. 1 and shows the linearity of the catalytic activity as a function of time at a second pH, pH 7, and that the preparation is still active after storage.

Approximately 0.064 mg of glucose isomerase-like modified protein is determined to be bound to each gram of swelled activated Sepharose-4B gel.

The quantity of modified glucose isomerase-like protein used in this assay is $4.0 \times 10^{-4}$ micromoles. From the calculated activity above, there is $5.07 \times 10^{-2}$ micromoles of fructose converted or turned over to glucose in 240 minutes. Therefore, approximately 127.9 micromoles of fructose is converted to glucose per micromole of glucose isomerase-like modified protein during the assay.

This identifies the above reaction as a catalytic process.

EXAMPLE 3

PART A

Partial Denaturation of Glucose Oxidase by Production of Apo Glucose Oxidase

Glucose oxidase is a flavin containing glycoprotein which catalyzes the oxidation of glucose to gluconic acid. The glycoprotein contains two moles of flavin-adenine dinucleotide (FAD) per mole of enzyme, and has a molecular weight of 160,000 consisting of two identical subunits. The apoenzyme of glucose oxidase prepared by the acid-ammonium sulfate method has the same molecular weight as the holoenzyme. This is reported in an article by: Swaboda, B. E. P., *Biochim. Biophys. ACTA*, 175 p. 365–379. He also showed that apoenzyme prepared by the acid-ammonium sulfate method has no glucose oxidase catalytic activity, but that incubating the apoenzyme with an excess of FAD the holoenzyme activity is regenerated. According to the same article: "It has been proposed that the apoenzyme exists in two forms, $P_1$ and $P_2$, which are probably in equilibrium with one another. The $P_1$ (80%) has a loose flexible foil structure and a molar frictional ratio of 2.2 at pH 5.6. The $P_2$ form (20%) has a more compact structure and a frictional ratio of 1.2." Thus, the structure of glucose oxidase is partially denatured by removal of the FAD portion of the enzyme.

The apoenzyme of glucose oxidase is prepared by removing the FAD of glucose oxidase using the method as described in the article: Tsuge, H. and Mitsuda, H., *The Journal of Vitaminology* 17, 24–31, (1971).

About 100 mg of glucose oxidase (type VII) from *Aspergillus niger*, purchased from Sigma Chemical Company, No. G-2133, Lot 88C-0064, is dissolved in 25 milliliters of 0.05 M sodium acetate buffer, pH 5.5 and ammonium sulfate granules are added slowly to bring the solution to 80% suturation. The glucose oxidase solution is kept at 0° C. during the course of this procedure. The pH of the solution is adjusted to 2.0 with 4 N HCl and allowed to stand for 30 minutes. The resulting precipitate is centrifuged at 27,000 g. for 30 minutes. The yellow supernatant is decanted and the slightly yellowish precipitate is dissolved in 2.5 milliliters of 2.0 M ammonium acetate. The resulting solution is added dropwise to 25 milliliters of acidic-85% saturated ammonium sulfate solution (pH 2.0 adjusted with 4 N HCl). Using the resulting precipitate, the above treatment is repeated two times so that the supernatant fraction appears colorless.

The above precipitate is dissolved in 3.5 milliliters of 0.05 M sodium acetate buffer, pH 5.5 and dialyzed against 0.05 M acetate sodium buffer, pH 5.5 for 17 hours using a dialysis tubing having a molecular weight cut-off of 12–14,000 daltons. The concentration of the dialyzed apoenzyme is determined in accordance with the teachings of D. M. Kirschenbaum in *Analytical Biochemistry* 82, pages 83–100, 1977. The absorbance at 280 nm is measured as 3.42. Using the absorbance coefficient value of 10.6, the concentration of the solution is about 3.23 milligrams per milliliter.

The activity of the native glucose oxidase and the apoenzyme is determined by the colorimetric determination of hydrogen peroxide produced during the coupled reaction with 0-dianisidine and peroxidase. This assay procedure is obtained from the *Worthington Enzyme Manual*, pages 19–20, 1972. The activity is expressed as units/milligram where one unit of glucose oxidase activity is that amount of enzyme liberating one micromole of $H_2O_2$ per minute at 25° C. The results of this assay shows that the apoenzyme has only 0.12% of the initial activity of the native glucose oxidase. This trace of activity is subsequently removed as described below.

PART B

Preparation of Immobilized Model Enzyme Inhibitor

A method of purifying this apoenzyme, that is, a method of removing all the native glucose oxidase activity, is developed in which the dialyzed apoenzyme of PART A is added to a cellobiose inhibitor gel affinity column. This procedure purifies the apoenzyme from the portion in PART A which still has native glucose oxidase activity and yields an apoenzyme fraction possessing no measurable glucose oxidase activity.

A glass walled chromatography column of about 5.0 cm length and about 1.5 cm interior diameter is used in the procedure. The immobilized glucose isomerase inhibitor, namely cellobiose, gel is prepared as follows. The inhibitor, cellobiose, is immobilized on a solid, organic, water insoluble support comprising an agarose based, linear, cross-linked polysaccharide having alternating residues of D-galactose and 3, 6 anhydro-L-galactose. The immobilization support is available from Pharmacia Fine Chemicals under the name Sepharose 4B Gel.

The column material is prepared in accordance with the process outlined by Sundberg and Porath in *J. of Chromatography* entitled "Preparation of Adsorbents for Biospecific Affinity Chromatography", 90, pg. 87–98 (1974). The procedure is as follows:

Twenty-five grams of Sepharose 4B Gel is washed on a glass filter-funnel with two liters of distilled deionized water and suction-dried for five minutes under vacuum. To the suction-dried gel is added 25 milliliters of 1,4 butanediol diglycidyl ether and 25 milliliters of 0.6 M NaOH containing two milligrams of sodium borohydride per milliliter of solution. The resulting suspension is shaken for five hours on an Eberbach shaker at low speed.

After five hours, the suspension is washed on a glass filter-funnel with 750 milliliters of distilled, deionized water; then 750 milliliters of 0.02 M sodium phosphate buffer, pH 7.5; 750 milliliters of 0.001 M tris-HCl buffer, pH 7.0; 750 milliliters of 0.02 M glycine-HCl buffer, pH 3.0 and finally 750 milliliters of 0.05 M sodium carbonate buffer, pH 10.0 and suction-dried for five minutes.

To the suction-dried gel is added 25 milliliters of a 2% D(+) cellobiose solution. The cellobiose solution is made from 500 mg of cellobiose in 25 milliliters of 0.05 M sodium carbonate buffer, pH 10 with the cellobiose from Sigma Chemical Co., No. C-7252, lot No. 110F-0656. The cellobiose-gel solution is shaken at slow speed for 16 hours.

After 16 hours, the suspension is washed on a glass filter-funnel with 750 milliliters of 0.05 M sodium carbonate buffer, pH 10.0; 750 milliliters of distilled deionized water; 750 milliliters of 0.001 M tris-HCl buffer, pH 7.0; 750 milliliters of 0.02M glycine-HCl, pH 3.0 and finlly 750 milliliters of 0.05M sodium carbonate buffer, pH 9.5. The gel is suction-dried under vacuum for five minutes.

Twelve and one-half grams of the suction-dried material is added to 20 milliliters of 2.0M ethanolamine solution. The ethanolamine reagent is made by adding 2.54 milliliters of 95% ethanolamine to sufficient 0.05M sodium carbonate buffer, pH 9.5, to make 20 milliliters volume. The gel-ethanolamine solution is shaken for five hours and then washed on a glass filter-funnel as follows, in the order given, 500 milliliters of 0.05M sodium carbonate buffer, pH 9.5; 500 milliliters of 0.02M sodium phosphate buffer, pH 7.5; 500 milliliters of 0.001M tris-HCl buffer, pH 7.0 and 500 milliliters of distilled deionized water. The gel is next suction-dried under vacuum, resuspended in distilled deionized water and stored under refrigeration until the column is packed.

To prepare the column for acceptance of the dialyzed apoenzyme, the column is packed about 3.8 centimeters high with immobilized cellobiose inhibitor gel. After packing the column, it is purged of possible contaminants by washing the column as follows: 200 ml of 0.001M tris-HCl buffer, pH 8.0; 200 ml of 0.05M sodium acetate buffer, pH 5.5; 150 ml of 2.0M guanidine HCl aqueous solution; and finally with 200 ml of 0.1M sodium phosphate buffer, pH 7.0.

PART C

Purification of Dialyzed Apoenzyme of Glucose Oxidase

The column of PART B is purged with a flowing stream of 0.1M sodium phosphate buffer, pH 7.0, flowing at 1.5 ml per minute. Two ml of dialyzed apoenzyme of PART A is injected at the head of the column. The eluant from the column is monitored at 254 nm. When that portion of the apoenzyme not binding to the immobilized cellobiose inhibitor eluted from the column, it is collected and determined to contain 1.8 milligrams of apoenzyme by using the method of D. M. Kirschenbaum described above. Accordingly, about 4.6 milligrams of apoenzyme is bound to the inhibitor on one exposure to the column.

A portion of the apoenzyme not binding to the cellobiose gel is assayed for glucose oxidase activity by the colorimetric determination of hydrogen peroxide produced during the coupled reaction of 0-dianisidine and peroxidase described above. All of the glucose oxidase activity (expressed as total units) in the ten milliliter sample of dialyzed apoenzyme added to the column is present in the portion of the apoenzyme not binding to the column. Therefore, the apoenzyme still bound to the column has no measurable glucose oxidase activity and has been purified by the affinity chromatography procedure.

PART D

Cross-linking

The 4.6 milligrams of inhibitor column bound apoenzyme which is devoid of any measurable native glucose oxidase activity is cross-linked with dimethyl suberimidate dihydrochloride purchased from Sigma Chemical Company, No. 7636, Lot 31F-0225. The cross-linking agent is prepared by dissolving 0.1 gram of dimethyl suberimidate dihydrochloride in 25 ml of 0.1M sodium phosphate buffer, pH 7.0. The outlet of the column of PART C is connected to the head of the column to form a closed recirculation flow loop. The 25 ml of cross-linking agent is recirculated through the column for about 90 minutes at a flow rate of 1.5 ml per minute.

The circulating cross-linking agent solution is found to contain approximately 2.0 milligrams of the enzyme-like modified protein originally bound to the column; thereby leaving 2.5 milligrams still bound.

PART E

Collection of the Enzyme-Like Modified Protein

The recirculating system of PART D is disconnected and a 0.1M sodium phosphate buffer, pH 7.0, is pumped through the column now containing the inhibitor-bound, cross-linked enzyme-like modified protein, at 1.5 ml per minute. Approximately two bed volumes (15 ml) of the pH 7.0 sodium phosphate buffer is pumped through the column to remove any excess dimethyl suberimidate dihydrochloride. Then a 0.05M glycine-HCl buffer, pH 3.0 is pumped through the column at 1.5 ml per minute. After about 10 minutes, modified protein began eluting from the column. About 25 ml of eluant is collected before the modified protein stopped eluting.

The absorbance at 280 nm is determined to be 0.027, thus, about 0.3 mg of modified protein is found to be collected.

The eluant is changed to 0.05M glycine-NaOH buffer, pH 9.5. After pumping this pH 9.5 glycine-NaOH buffer through the column at a flow rate of 1.5 ml per minute for five minutes, modified protein began eluting from the column. About 25 ml of eluant is collected before the modified protein stopped eluting. The absorbance at 280 nm is determined as in PART A to be 0.082, thus about 1.95 milligrams of modified protein is found to be collected.

PART F

Results

The following activity with respect to fructose substrate for glucose isomerase is recorded from a sample of the glucose isomerase-like modified protein prepared according to the invention in PARTS A-E above.

A portion of the eluant collected in PART E is analyzed for glucose isomerase enzymatic activity as follows: The activity is determined colorimetrically using a Sigma Chemical Company Glucose Diagnostic Kit No. 510-A by measuring the amount of glucose generated from fructose as a function of time.

The procedure is based on the coupled enzymatic reactions of glucose oxidase and peroxidase with ortho-dianisidine as a chromagen. The intensity of the brown color measured at 450 nm is proportional to the glucose concentration.

The reaction solution is prepared as follows: 2.0 ml of glucose isomerase-like modified protein of PART E, collected at pH 9.5, and 2.0 ml of 0.1M beta-D fructose substrate for glucose isomerase in 0.05M sodium acetate buffer, pH 5.5 are admixed.

The control solution No. 1 is prepared by mixing 2.0 ml of glucose isomerase-like modified protein of PART E, collected at pH 9.5 with 2.0 ml of 0.05M sodium acetate buffer, pH 5.5.

The control solution No. 2 is prepared by mixing 2.0 ml of 0.05M glycine-NaOH buffer, pH 9.5 with 2.0 ml of 0.1M beta-D fructose substrate in 0.05M sodium acetate buffer, pH 5.5.

The final pH of both controls and the reaction solution is 8.1.

The reaction solution, control No. 1 and control No. 2 are placed in a 37° C. water bath and gently shaken. After incubating at 37° C. for 5 minutes, 15 minutes, 30 minutes, 45 minutes, 60 minutes and 90 minutes; 0.5 ml of each solution is removed and added to 1.0 ml of a solution containing glucose oxidase, peroxidase and ortho-dianisidine (PGO). The PGO reaction is allowed to proceed to completion in approximately 30 minutes at 37° C., and then the absorbance at 450 nm is measured on a Cary 14 spectrophotometer.

For each time interval, the change in absorbance is calculated by subtracting the absorbance of control No. 1 and control No. 2 from the absorbance of the reaction solution and then adding the absorbance of 1.0 ml of PGO solution added to 0.25 ml of 0.05M glycine-NaOH buffer, pH 9.5 and 0.25 ml of 0.05M sodium acetate buffer, pH 5.5, i.e. Reaction solution—control No. 1—control No. 2+PGO and buffer=change in absorbance.

Then using the calculated change in absorbance for each time interval listed above, a linear regression analysis is performed. The resulting slope (change in absorbance per min.) is used in the following equation to calculate the activity in units per gram glucose isomerase-like modified protein.

$$\text{Units/g} = \frac{(\text{change } A/\text{min.}) \ (SV) \ (k)}{(MP)}$$

Wherein: MP is grams of enzyme-like modified protein in the reaction mixture; k is 0.343 micromoles per milliliter-absorbance, the constant calculated from a plot of known glucose standards versus the change in absorbance as determined by the Sigma Glucose Diagnostic Kit No. 510-A;

change $A/\text{min.}$ is the change in absorbance per minute; and

SV is sample volume in milliliters.

The modified protein eluted at pH 3.0 had no detectable glucose isomerase activity.

The calculated activity from the 37° C. assay results for the glucose isomerase-like modified protein eluted at pH 9.5 is as follows:

| | SUBSTRATE Fructose (Activity in Units/gram) |
|---|---|
| Apo glucose oxidase | 0.0 |
| Enzyme-like modified protein | 5.3 ± 0.2 |

Figure 3:
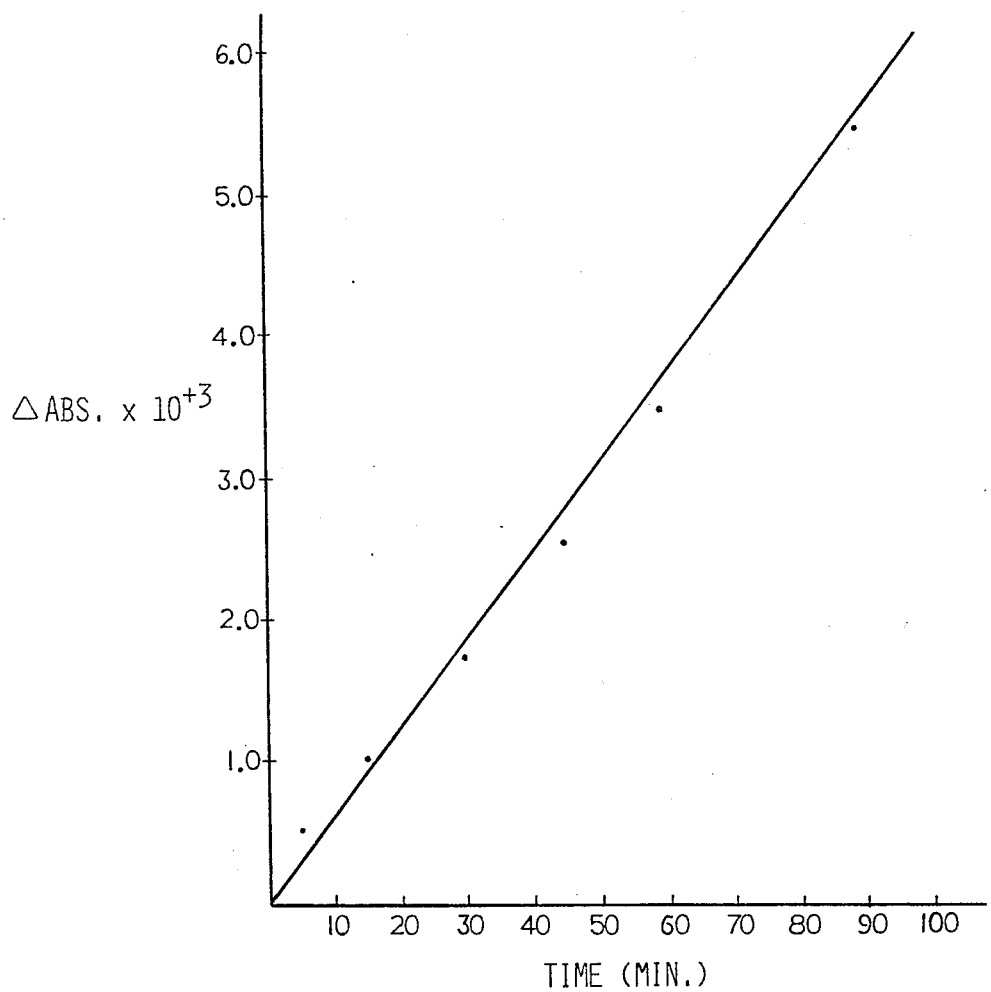
FIG. 3 illustrates the catalytic activity of the enzyme-like modified protein prepared in Example 3.

The results show that the glucose isomerase-like modified protein of PART E exhibits catalytic activity with respect to glucose isomerase substrate, fructose, where no glucose isomerase activity is previously detected in the native glucose oxidase starting material. The activity data measured above is illustrated graphically at FIG. 3 and shows the linearity of the catalyic activity as a function of time. The quantity of glucose isomerase-like modified protein used in this assay is $9.6 \times 10^{-4}$ micromoles.

From the calculated activity above, there is $7.36 \times 10^{-2}$ micromoles of fructose converted or turned over to glucose in 90 minutes.

Therefore, approximately 76 micromoles of fructose substrate is converted to glucose per micromole of glucose isomerase-like modified protein during the assay.

This identifies the above reaction as a catalytic process due to the measured turnover rate disclosed above.

This Example illustrates the conversion of glucose oxidase, an enzyme of the oxido-reductase group, to a glucose isomerase-like modified protein. Glucose isomerase is a member of the isomerase group of enzymes.

EXAMPLE 4

PART A

Partial Denaturation of Concanavalin A by Production of Apo Concanavalin A

Concanavalin A-2X (hereinafter Con A) is purchased from ICN Nutritional Biochemicals as Cat No. 101410, Lot 1981. Fifty mg of the Con A as purchased is dissolved in 100 ml of distilled, deionized water. The pH of this solution is adjusted to 3.0 by the slow addition of concentrated acetic acid. The solution of Con A, thus adjusted to pH 3.0 is stirred slowly at room temperature for one hour, and then dialyzed against a solution of acetic acid, pH 3.0, in a Spectrapor brand dialysis tube membrane No. 2, having a molecular weight cut-off 12–14,000 daltons, at 5° C., for 24 hours. The dialysate is changed twice during this period. This procedure results in the demetallized partially denatured apoprotein form of Con A, (Ref: J. W. Becker, et al., Nature 259, 406–409, 1976).

PART B

Addition of Inhibitor

The above solution of demetallized, partially denatured apo Con A is admixed with an inhibitor of glucose isomerase, namely D-mannitol (purchased from Sigma Chemicals Co. as Cat. No. M-4125, Lot 81 F-0517). A 2% solution of D-mannitol is prepared in water, and 2 ml of this solution is added dropwise to the apo Con A solution. The apo Con A solution containing the inhibitor is stirred at room temperature for two hours.

PART C

Cross-linking

The solution of partially denatured apo Con A containing inhibitor from PART B above is divided into two 100 ml portions. One portion is maintained at pH 3.0, while the pH of the other portion is raised to 7.0 by the addition of 0.1M NaOH. To both the solutions is added 400 microliters of 8% glutaraldehyde cross-linking agent (purchased from Polyscience as Cat No. 0216) and the solutions are stirred at 5° C. for six hours. The solutions of cross-linked Con A solutions are dialyzed against 0.001M sodium acetate buffer, pH 5.0, for 48 hours, with six changes in the dialysate. The solutions are then lyophilized and stored at −60° C. until assay for glucose isomerase activity present in the glucose isomerase-like modified protein is done.

PART D

Results

The assay for glucose isomerase activity in the glucose isomerase-like modified Con A is as follows:

Glucose isomerase activity is assayed, using beta-D fructose (as reference grade from Pfanstiel Labs, Cat. No. RF G 100, Lot 14166) as the substrate and measuring the glucose formed by a Glucose Oxidase-peroxidase (PGO) method as disclosed by Kesdan A. S., *Abstracts* 129 meeting ACS, p-31 C., 1956.

The following reagents are purchased from Sigma Chemical Company:

PGO-enzyme: Stock No. 510-6. Each preweighed capsule contains 500 units of glucose oxidase and 100 units of peroxidase and buffer salts. One such capsule is reconstituted by dissolving it in 20 ml of distilled water by gentle shaking and storing in amber colored flasks until used.

Ortho-dianisidine hydrochloride: Stock No. 510-50. Preweighed vials containing 50 mg of this chromogen is reconstituted in 10 ml of distilled water.

A combined enzyme-color reagent is prepared by mixing 20 ml of the PGO enzyme solution with 0.15 ml of the chromogen, by mild stirring.

A standard curve for glucose is constructed by the following procedure:

Sigma Chemical Company glucose standard solution (Stock 635-100) containing 5.56 millimoles of glucose per liter is diluted 1 to 100 with distilled water to obtain a solution containing 0.0556 micromoles of glucose per ml. Aliquots of 50, 100, 150 and 200 microliters of this solution are pipetted into clean glass tubes, and the volumes are equalized to 200 microliters by adding necessary volumes of distilled water. A blank tube containing 200 microliters of distilled water and no glucose is also set up. To each tube is added one ml of the PGO-color reagent. Contents of the tubes are mixed well and incubated at 37° C. for 10 minutes. The absorbance readings at 450 mu are recorded in a Cary 15 spectrophotometer with water in the reference cell. Absorbance of the blank is subtracted from the sample readings, and a standard curve is plotted with the known glucose concentrations in the X-axis, vs. the optical density at 450 mu in the Y-axis.

To determine the glucose isomerase activity in the glucose isomerase-like modified protein, the sample and control assay solutions are made up as follows:

Sample: Substrate solution is made up by dissolving 9 mg of fructose substrate in one ml of 0.05M sodium acetate buffer, pH 6.0. The lyophilized powder of modified protein from PART C above is also dissolved in the same buffer and protein concentration is determined by measuring the optical density at 280 mu, and using the standard absorbance value of a 1% Con A solution as 12.4 as disclosed by Kirschenbaum, D. M. 1972, in *Int. J. Protein. Res.*, 4, 63–73. One hundred microliters of the fructose substrate solution is mixed with 100 microliters of the glucose isomerase-like protein. Four such tubes containing the mixtures of fructose and enzyme are prepared. Incubations are done at 37° C. for varying periods of time. Glucose formed during the incubation is determined by the PGO method described above.

Control: For the control experiments, the fructose substrate solution and the modified protein solution are incubated separately, and at the end of a particular incubation period, 100 microliters of each solution is mixed, and PGO reaction done as in the case of the sample.

The difference in the optical density at 450 mu, between the sample and the control is calculated and the glucose formed due to the glucose isomerase-like activity in the glucose isomerase-like modified protein is determined from the standard glucose curve described above. The units of activity is expressed as the micromoles of glucose formed per min. per gram of protein.

The difference in the optical density at 450 mu between the sample and the control is computed and the amount of glucose produced is calculated from the standard values. The experiment is done for four different incubation periods, and the activity calculated by linear regression analysis.

The assay results are as follows:

|  | SUBSTRATE<br>Fructose<br>(Activity in Units/gm ±<br>standard deviation) |
| --- | --- |
| Native Con A | −.23 ± .04 |
| Native Con A contacted with<br>inhibitor but not cross-linked | −0.5 ± .1 |
| Enzyme-like Modified<br>Protein prepared at pH 3.0 | 0.84 ± .02 |
| Enzyme-like Modified<br>Protein Prepared at pH 7.0 | 1.30 ± .02 |

This illustrates the conversion of a nonenzymatic protein, namely concanavalin A, into an enzyme-like modified protein having glucose isomerase type activity. Glucose isomerase is an enzyme of the isomerase group.

EXAMPLE 5

PART A

Partial Denaturation of Concanavalin A by Production of Apo Concanavalin A

Concanavalin A-2X (hereinafter Con A) is purchased from ICN Nutritional Biochemicals as Cat No. 101410, Lot 1981. Twenty-five mg of the Con A as purchased is dissolved in 200 ml of distilled, deionized water. The pH of this solution is adjusted to 3.0 by the slow addition of concentrated acetic acid. The solution of Con A, thus adjusted to pH 3.0 is stirred slowly at room temperature for one hour, and then dialyzed against a solution of acetic acid, pH 3.0, in a Spectrapor brand dialysis tube membrane No. 2, having a molecular weight cutoff 12–14,000 daltons, at 5° C., for 24 hours. The dialysate is changed twice during this period. This procedure results in the demetallized partially denatured apoprotein form of Con A, (Ref: J. W. Becker, et al., *Nature* 259, 406–409, 1976).

PART B

Addition of Inhibitor

The above solution of demetallized, partially denatured apo Con A is admixed with an inhibitor of glucose isomerase, namely D-mannitol (purchased from Sigma Chemicals Co. as Cat. No. M-4125, Lot 81 F-0517). A 2% solution of D-mannitol is prepared in water, and one ml of this solution is added dropwise to the apo Con A solution. The apo Con A solution containing the inhibitor is stirred at room temperature for two hours.

PART C

Cross-linking

The pH of the solution from PART B is raised to 7.4 by the addition of 0.1 N NaOH, and 1.5 ml of a 1% solution of dimethyl suberimidate dihydrochloride cross-linking agent (purchased from Sigma Chemical Co., Cat. No. D-7636, Lot 31 F-0225) is added. The partially denatured Con A is stirred with the cross-linking agent for 6 hours, at 5° C., and then dialyzed against distilled water for 48 hours, with 6 changes of the dialysate. The dialyzed solution is lyophilized and stored at −60° C., until assay for glucose isomerase-like activity is performed on the lyophilized material.

PART D

Results

The assay for glucose isomerase activity in the glucose isomerase-like modified Con A is as follows:

Glucose isomerase activity is assayed, using beta-D fructose (reference grade from Pfanstiel Labs, Cat. No. RF G 100, Lot 14166) as the substrate and measuring the glucose formed by a Glucose Oxidase-peroxidase (PGO) method as disclosed by Kesdan A. S., *Abstracts* 129 meeting ACS, p-31 C., 1956.

The following reagents were purchased from Sigma Chemical Company:

PGO-enzyme: Stock No. 510-6. Each preweighed capsule contains 500 units of glucose oxidase and 100 units of peroxidase and buffer salts. One such capsule is reconstituted by dissolving it in 20 ml of distilled water by gentle shaking and storing in amber colored flasks until used.

O-dianisidine hydrochloride: Stock No. 510-50. Preweighed vials containing 50 mg of this chromogen is reconstituted in 10 ml of distilled water.

A combined enzyme-color reagent is prepared by mixing 20 ml of the PGO enzyme solution with 0.15 ml of the chromogen, by mild stirring.

A standard curve for glucose is constructed by the following procedure:

Sigma Chemical Company glucose standard solution (Stock 635-100) containing 5.56 millimoles of glucose per liter is diluted 1 to 100 with distilled water to obtain a solution containing 0.0556 micromoles of glucose per ml. Aliquots of 50, 100, 150 and 200 microliters of this solution is pipetted into clean glass tubes of volume equalized to 200 microliters by adding necessary volumes of distilled water. A blank tube containing 200 microliters of distilled water is also set up. To each tube is added one ml of the PGO-color reagent. Contents of the tubes are mixed well and incubated at 37° C. for 10 minutes. The absorbance readings at 450 mu are recorded in a Cary 15 spectrophotometer with water in the reference cell. Absorbance of the blank is subtracted from the sample readings, and a standard curve is plotted with the known glucose concentrations in the X-axis, vs. the optical density at 450 mu in the Y-axis.

To determine the glucose isomerase activity in the glucose isomerase-like modified Con A protein, the sample and the control assay solutions are made up as follows:

Sample: Lyophilized modified Con A protein from PART C is dissolved in 0.1M sodium acetate buffer pH 4.5. The protein concentration is determined by measuring the optical density at 280 mu and using the standard absorption value of 12.4 for a 1% solution of Con A native protein as disclosed by Kirschenbaum, D. M. in *Int. J. Protein Res.* 4, 63 (1972).

One hundred microliters of fructose substrate solution (0.05M of reference grade fructose in 0.1M acetate buffer pH 4.5) is combined with 50 microliters of the same buffer, and 50 microliters of the modified Con A protein solution containing 48 microgram of protein. Four such tubes containing the substrate, buffer and the modified protein are prepared. Incubations are done at 37° C. for various periods, and the glucose generated measured by the PGO method.

Control: Control mixtures consist of 100 microliters of fructose and 50 microliters of the above buffer together, and to which 50 microliters of a separately incubated solution of modified Con A protein solution is added at the end of the incubation period. The PGO reaction is done as for the sample solution above.

The difference in the optical density at 450 mu between the sample and the control is computed. After obtaining 4 such values at different periods of incubation, the micromoles of glucose formed per minute per gram of enzyme-like modified protein is calculated by the linear regression analysis.

| | SUBSTRATE<br>Fructose<br>(Activity in Units/gm ±<br>standard deviation) |
| --- | --- |
| Native Con A | −0.23 ± 0.04 |
| Enzyme-like Modified Protein | 1.32 ± 0.07 |

This illustrates the conversion of a nonenzymatic protein, namely concanavalin A, into an enzyme-like modified protein having glucose isomerase type activity. Glucose isomerase is an enzyme of the isomerase group.

EXAMPLE 6

PART A

Partial Denaturation of Concanavalin A by Production of Apo Concanavalin A

Concanavalin A-2X (hereinafter Con A) is purchased from ICN Nutritional Biochemicals as Cat No. 101410, Lot 1981. Fifty mg of the Con A as purchased is dissolved in 100 ml of distilled, deionized water. The pH of this solution is adjusted to 3.0 by the slow addition of concentrated acetic acid. The solution of Con A, thus adjusted to pH 3.0 is stirred slowly at room temperature for one hour, and then dialyzed against a solution of acetic acid, pH 3.0, in a Spectrapor brand dialysis tube membrane No. 2, having a molecular weight cut-off 12–14,000 daltons, at 5° C., for 24 hours. The dialysate is changed twice during this period. This procedure results in the demetallized partially denatured apo-protein form of Con A, (Ref: J. W. Becker, et al., *Nature* 259, 406–409, 1976).

PART B

Addition of Inhibitor

The above solution of demetallized, partially denatured apo Con A protein is admixed with an inhibitor of glucose isomerase, namely D-mannitol (purchased from Sigma Chemicals Co. as Cat. No. M-4125, Lot 81 F-0517). A 2% solution of D-mannitol is prepared in water, and 2 ml of this solution is added dropwise to the apo Con A protein solution. The apo Con A protein solution containing the inhibitor is stirred at room temperature for two hours.

PART C

Cross-linking

The pH of the solution from PART B above containing partially denatured Con A protein solution containing the inhibitor is raised to 7.0, by the addition of 0.1M NaOH and 400 microliters of 8% glutaraldehyde cross-linking agent (purchased at Polyscience as Cat. No. 0216) is added to this solution. The partially denatured Con A protein is stirred with the cross-linking agent for 6 hours at 5° C., and then dialyzed against distilled water for 48 hours, with 6 changes of the dialysate. The material is then lyophilized, and stored at -60° C., until assay for glucose isomerase activity is done.

PART D

Results

The assay of the modified Con A protein for glucose isomerase-like activity at different pH values to determine the pH dependence of the glucose isomerase-like modified protein activity is as follows.

Sodium acetate buffers (0.1M) of pH values ranging from 4.0 to 6.0 and sodium phosphate buffers (0.1M) of pH values 6.0–8.0 are prepared by mixing the necessary solutions in proper proportions, as described in *Methods in Enzymology* Vol. 1, ed. S. P. Colowick and N. O. Kaplan, pages 140 and 143 (1955). The final pH of each buffer is confirmed by a pH meter.

Next, about 4 mg of lyophilized modified Con A protein from PART C above is dissolved in 1 ml of distilled, deionized water, and aliquots of the solution is diluted 1 to 5 with each of the above buffers.

Fructose substrate for the glucose isomerase reaction is prepared by dissolving 36 mg of reference grade fructose (purchased from Pfanstiel Labs, Cat. No. RFG 100, Lot 14166) in one ml of water, thus obtaining a 0.2M solution.

The sample assay is as follows: Fifty microliters of the fructose solution from above is combined with 100 microliters (48 microgram protein) of the modified Con A protein solution, and fifty microliters of the appropriate buffer. Separate incubation is done for each pH value. Final pH of the assay solution is checked, and the assay mixture is incubated at 37° C. for 30 minutes. The glucose generated is determined by the PGO method disclosed in Example 6 above and disclosed in the reference by Kesdan, A. S., *Abstracts*, 129 Meeting ACS, p. 31C (1956).

Control assay: For control assays, 50 microliters of the fructose solution is incubated with the appropriate buffers. The solution of the modified Con A protein is incubated in a separate tube, and 100 microliters of this is added to the fructose solution at the end of the incubation period. The PGO reaction is done as for the sample.

Figure 4:
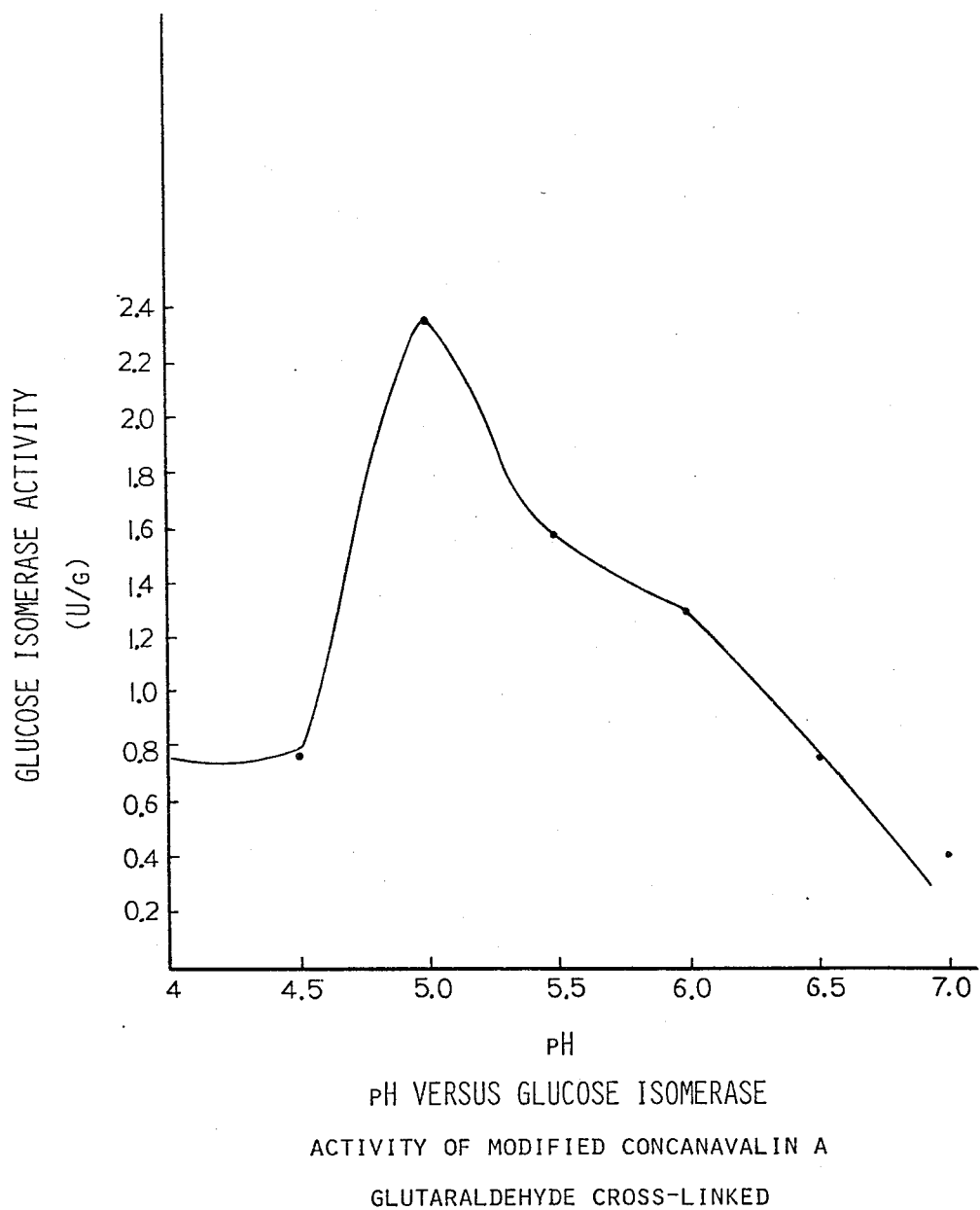
FIG. 4 illustrates the catalytic activity of the enzyme-like modified protein prepared in Example 6 as a function of pH.

The amount of glucose generated by the glucose isomerase-like activity in the modified Con A protein is computed from the difference in the absorbance at 450 mu between the sample and the control and from the known absorbance values for the standard glucose. The pH optimum curve observed in the presence of the glucose isomerase-like modified protein is constructed by plotting the pH values against the micromoles of glucose formed per minute per gram protein. The graphical pH dependence is illustrated in FIG. 4. Such pH dependence of a reaction is typical of an enzyme catalyzed reaction.

The following activity for glucose isomerase-like modified protein prepared as described above is obtained at various pH values as reported below.

| Enzyme-like Modified Protein at pH | SUBSTRATE<br>Fructose<br>(Activity in Units/gram) |
| --- | --- |
| 4.0 | 0.78 |
| 4.5 | 0.78 |
| 5.0 | 2.33 |
| 5.5 | 1.56 |

-continued

| Enzyme-like Modified Protein at pH | SUBSTRATE Fructose (Activity in Units/gram) |
| --- | --- |
| 6.0 | 1.29 |
| 6.5 | 0.78 |
| 7.0 | 0.39 |
| 7.5 | — |
| 8.0 | — |

The glucose isomerase-like modified protein activity with respect to a glucose isomerase substrate generated from the nonenzymatic Con A by the process of the present invention gives a bell-shaped pH profile, which is a typical characteristic of a true enzyme catalyzed reaction, and is illustrated graphically at FIG. 4 showing activity as a function of pH. This illustrates the conversion of a nonenzymatic protein, namely concanavalin A, into an enzyme-like modified protein having glucose isomerase type activity. Glucose isomerase is an enzyme of the isomerase group.

EXAMPLE 7

PART A

Partial Denaturation of Concanavalin A by Production of Apo Concanavalin A

Concanavalin A-2X (hereinafter Con A) is purchased from ICN Nutritional Biochemicals as Cat No. 101410, Lot 1981. Twenty-five mg of the Con A as purchased is dissolved in 200 ml of distilled, deionized water. The pH of this solution is adjusted to 3.0 by the slow addition of concentrated acetic acid. The solution of Con A, thus adjusted to pH 3.0 is stirred slowly at room temperature for one hour, and then dialyzed against a solution of acetic acid, pH 3.0, in a Spectrapor brand dialysis tube membrane No. 2, having a molecular weight cut-off 12-14,000 daltons, at 5° C., for 24 hours. The dialysate is changed twice during this period. This procedure results in the demetallized partially denatured apoprotein form of Con A protein, (Ref: J. W. Becker, et al., Nature 259, 406-409, 1976).

PART B

Addition of Inhibitor

The above solution of demetallized, partially denatured apo Con A protein is admixed with an inhibitor of glucose isomerase, namely D-mannitol (purchased from Sigma Chemicals Co. as Cat. No. M-4125, Lot 81 F-0517). A 2% solution of D-mannitol is prepared in water, and 1 ml of this solution is added dropwise to the apo Con A protein solution. The apo Con A protein solution containing the inhibitor is stirred at room temperature for two hours.

PART C

Cross-linking

The pH of the above solution is raised to 7.4 by the addition of 0.1N NaOH, and 1.5 ml of a 1% solution of dimethyl suberimidate dihydrochloride cross-linking agent (purchased from Sigma Chemicals Co. as Cat. No. D-7636, Lot 31 F-0225) is added. The partially denatured Con A protein is stirred with the cross-linking agent for 6 hours, at 5° C., and then dialyzed against distilled water for 48 hours, with 6 changes of the dialysate. The solution in the dialysis bag is lyophilized and stored at −60° C., until assay for glucose isomerase-like activity is done on the lyophilized material.

PART D

Results

The assay of the modified Con A protein for glucose isomerase-like activity at several pH values to determine the pH dependence of the glucose isomerase-like modified protein is as follows.

Sodium acetate buffers (0.1M) of pH values ranging from 4.0 to 6.0 and sodium phosphate buffers (0.1M) of pH values 6.0-8.0 are prepared by mixing the necessary solutions in proper proportions as described in *Methods in Enzymology*, Vol. 1, ed. S. P. Colowick and N. O. Kaplan, pages 140 and 143 (1955). The final pH of each buffer is confirmed by a pH meter.

Next about 12 mg of lyophilized modified Con A protein from PART C above is dissolved in 2 ml of distilled, deionized water, and aliquots of the solution is diluted 1 to 5 with each of the above buffers.

Fructose substrate for the glucose isomerase activity assay reaction is prepared by dissolving 36 mg of reference grade fructose in 1 ml of water, thus obtaining a 0.2M solution.

The sample assay is as follows: Fifty microliters of the fructose solution from above is combined with 50 microliters (30 microgram protein) of the modified Con A solution, and 100 microliters of the appropriate buffer. Separate incubation is done for each pH value. The final pH of the assay solution is checked, and the assay mixture is incubated at 37° C. for 30 minutes. The glucose generated is determined by the PGO method disclosed in Example 6 above and disclosed in the reference by Kesdan, A. S., *Abstracts,* 129 Meeting ACS, Pg. 31c (1956).

The control assay is as follows: For control assays, 50 microliters of the fructose solution is incubated with the 100 microliters of appropriate buffers. The solution of the modified Con A protein is incubated in a separate tube, and 50 microliters of this is added to the fructose solution at the end of the incubation period. The PGO reaction is done as for the sample.

Figure 5:
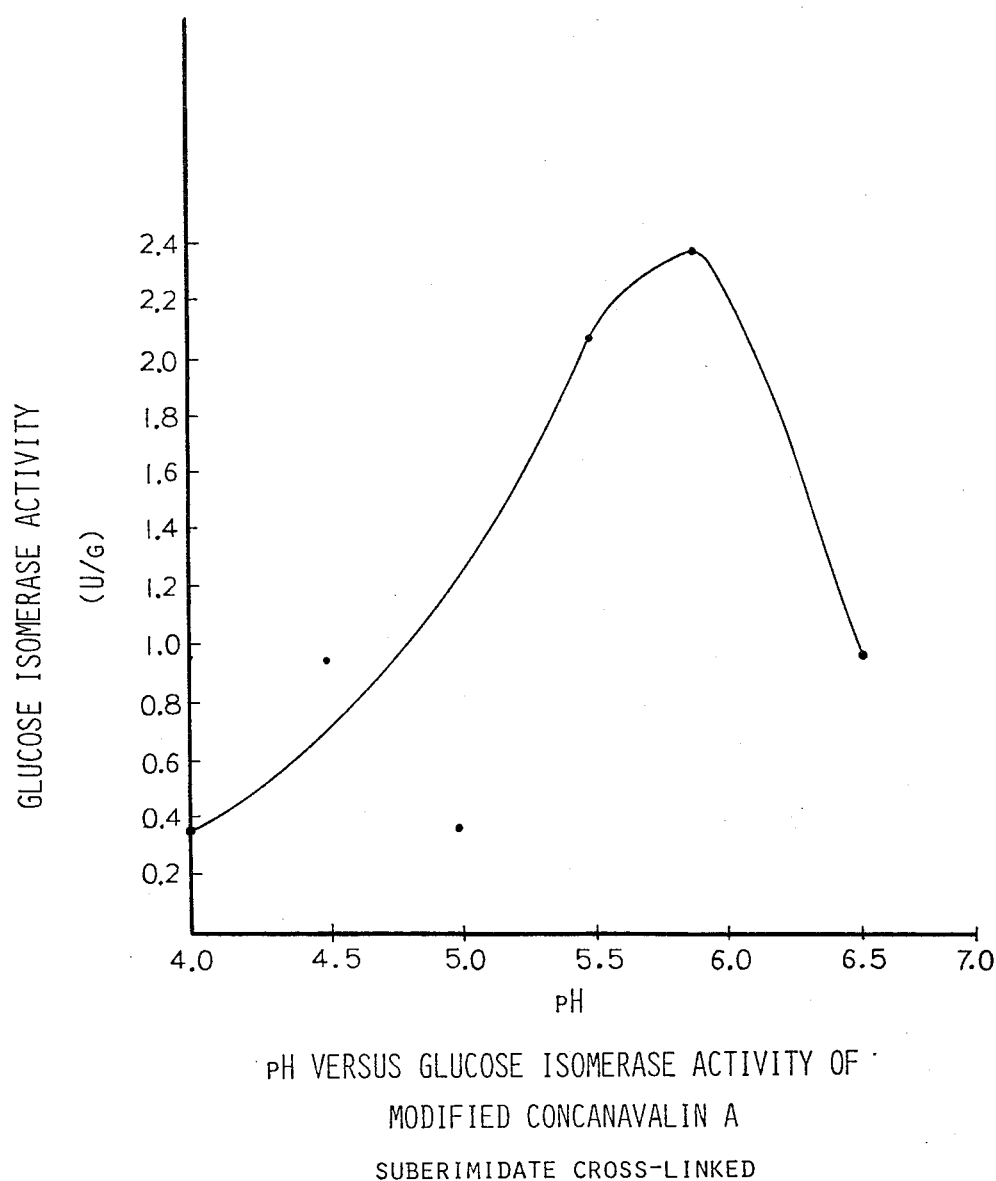
FIG. 5 illustrates the catalytic activity of the enzyme-like, modified protein prepared as Example 7 as a function of pH.

The amount of glucose generated by the glucose isomerase-like activity in the modified Con A protein is computed from the difference in the absorbance at 450 mu between the sample and the control and from the known absorbance values for the standard glucose. The pH optimum curve description of the enzymatic catalysis found in the glucose isomerase-like modified protein is constructed by plotting the pH values against the micromoles of glucose formed per minute per gram protein. Such graphical pH dependence is illustrated in FIG. 5. Such pH dependence of a reaction is typical of an enzyme catalyzed reaction.

The following activities for glucose isomerase-like modified protein prepared as described in this example is obtained, when the modified Con A having glucose isomerase activity is assayed pH values from 4.0 to 7.0.

| Enzyme-like Modified Protein at pH | SUBSTRATE Fructose (Activity in Units/gram) |
| --- | --- |
| 4.0 | 0.37 |
| 4.5 | 0.93 |
| 5.0 | 0.37 |
| 5.5 | 2.05 |

| Enzyme-like Modified Protein at pH | SUBSTRATE Fructose (Activity in Units/gram) |
|---|---|
| 6.0 | 2.25 |
| 6.5 | 0.93 |
| 7.0 | — |

The glucose isomerase-like modified protein catalytic activity with respect to glucose isomerase substrate present in the modified Con A protein prepared by the process of the present invention gives a bell-shaped curve with an optimum about the pH 6.0. This is characteristic of a typical enzyme catalyzed reaction, and is illustrated graphically at FIG. 5 showing the activity as a function of pH. This illustrates the conversion of a nonenzymatic protein, namely concanavalin A, into an enzyme-like modified protein having glucose isomerase type activity. Glucose isomerase is an enzyme of the isomerase group.

EXAMPLE 8

PART A

Partial Denaturation of Tryptophanase by Production of Apotryptophanase

The enzyme tryptophanase (L-tryptophan-indole lyase EC 4.1.99.1) catalyzes the deaminating degradation of L-tryptophan to indole, pyruvic acid and ammonia. Pyridoxal phosphate is an essential cofactor for this reaction. Holotryptophanase contains four identical subunits, each with a coenzyme binding site. Resolution of the coenzyme can be done by incubating the holotryptophanase with pyridoxal phosphate-binding agents such as penicillamine, (see T. Nihira et al., *J. App. Biochem.* 3, 212, 1981. Conversion of the holoenzyme to apoenzyme results in conformational perturbation so as to partially denature the tryptophanase protein as disclosed by the Ref. E. S. Snell, *Adv. in Enz.* Vol. 42, A. Meister ed. 287, 1975.

Preparation of the partially denatured apotryptophanase is as follows: Tryptophanase (L-Tryptophan-indole lyase, deaminating, Cat. No. T-0754, Lot 129C-6840) is purchased from Sigma Chemical Company. Twenty-five mg. of this enzyme is dissolved in 50 ml. of 0.1M potassium phosphate buffer pH 8.0. To this solution is added 90 mg. of penicillamine hydrochloride (Sigma Chemicals, Cat. No. P-5000, Lot 42 F-5013). The final concentration of penicillamine in the solution is 10 mM. The solution of tryptophanase containing penicillamine is incubated at room temperature for one hour, and then dialyzed for 48 hours against three liters of 0.01M potassium phosphate buffer, pH 8.0. The dialysate is changed four times during this period.

As a control, a solution of holotryptophanase (25 mg/50 ml of 0.1M potassium phosphate pH 8.0) is also dialyzed as above, without any prior incubation with penicillamine.

PART B

Addition of Inhibitor

Modification of both the apotryptophanase and the control holotryptophanase is done using an esterase-inhibitor, namely indole.

To the dialyzed solutions of apotryptophase, and holotryptophanase prepared as in the previous section, is added 25 mg. of solid indole inhibitor (Sigma Chemical Co. Cat. No. I-0750, Lot 119C-0124), and the solutions are stirred at room temperature for three hours to dissolve the inhibitor.

PART C

Cross-linking

The temperature of the partially denatured apoprotein solution, and the control tryptophanase solution is lowered to 5° C. in a shaking water bath, and 200 microliters of glutaraldehyde cross-linking agent (Polysciences, Cat. No. 0216) is added to each solution. The protein in each solution is cross-linked at 5° C. overnight for about 17 hours. The partially denatured cross-linked apotryptophanase and the similarly treated holotryptophanase are dialyzed against distilled water for 48 hours, with six changes of the dialysate. The dialyzed protein solutions are lyophilized and the powder stored at −60° C., until assay for esterase activity is performed.

PART D

Results

Esterase activity present in the above-modified proteins is assayed using L-tryptophan ethyl ester (L-TrEE) as substrate. The reaction is measured by determining the ethanol released during the esterolysis of the substrate using the ethanol assay-kit from Sigma Chemicals. The principle of the reaction is as follows:

The enzyme alcohol dehydrogenase (ADH) oxidizes ethanol to aldehyde, in presence of the cofactor-nicotinamide-adenine dinucleotide (NAD). During the reaction, NAD is reduced to NADH. This reduction of NAD to NADH results in a significant increase in the optical density at 340 mu, which is proportional to the concentration of ethanol in the reaction mixture. Thus the assay for esterase activity is performed by measuring the increase in the optical density at 340 mu, when the reaction is coupled with the NAD-ADH system.

Reagents for the ethanol determination are purchased from Sigma Chemical Co. in the form of ethanol assay kit. The kit contains the following reagents.

A. NAD-ADH vials (Stock No. 332-5) which has 9 micromoles of NAD and 750 Units of ADH.

B. Ethanol standard solution containing 0.08% ethanol Stock No. 330-20).

C. Glycine buffer reagent, which is a solution of 500 mM glycine buffer pH 9.0, with an aldehyde trapping agent. The NAD-ADH vial is reconstituted in one ml of glycine buffer, just prior to use.

The NAD-ADH reaction is calibrated as follows using the ethanol standard solution. The 4.6 ml of the 0.08% solution is diluted with distilled water to 8 ml which gives an ethanol solution of 10 mM (w/v). This solution is further diluted with water to obtain ethanol solutions of various concentrations ranging from 0.2 to 1 mM. One hundred microliters of this solution are pipetted into a spectrophotometer cell containing 0.9 ml. of glycine buffer and 0.1 ml of NAD-ADH solution. The initial absorbance of this solution at 340 mu increases upon the introduction of ethanol, and reaches a maximum. This optimal increase in absorbance at 340 mu after the addition of ethanol is plotted against the ethanol concentration, to obtain the standard curve. For the assay of the esterase activity in the enzyme-like modified proteins preparations, the following solutions are made:

a. 0.1 M tris-acetate buffer pH 7.5 b. L-tryptophan ethyl ester hydrochloride 0.1 M, obtained by dissolving 268 mg of the Sigma Product No. T-8755, Lot 101 F-5034 in 10 ml of the above tris buffer.

c. Enzyme-like modified protein: Lyophilized powders of the modified apo and holotryptophanase are dissolved in 5 ml of a and centrifuged to remove some insoluble residues. The protein concentrations of the supernatant solutions are determined by measuring the optical density at 280 mu, and using the standard absorbance of 7.95 for a 1% solution of tryptophanase (Ref. Kirschenbaum D. *Anal. Chem.*, 80, 193, 1977).

The modified apo and holotryptophanase is found to have the protein concentrations of 1.13 and 1.23 mg per ml, respectively. Incubation mixtures for the esterase assay:

1. Sample assay: This consists of 1.0 ml of a, 0.5 ml of b, and 0.5 ml of c (either apo or holo).
2. Blank I: This blank is done to measure the non-enzymatic hydrolysis of L-TrEE, and the assay mixture contains 1.5 ml of a and 0.5 ml of b.
3. Blank II: This blank is done to measure any possible absorbance increase due to the modified proteins alone without substrate, and contains 1.5 ml of a and 0.5 ml of c.

Incubation of the assay solutions is done at room temperature. Periodically, 0.5 ml of the assay mixtures are pipetted out and delivered into a test-tube containing 0.5 ml of glycine buffer pH 9.0, and to this mixture is added 0.1 ml of NAD-ADH mixture; (one vial dissolved in 1 ml of glycine buffer). The combined solutions are mixed and incubated at room temperature for 5 minutes and the optical density at 340 mu recorded in a Cary 15 spectrophotometer. The increase in absorbance at 340 mu due to the sample is calculated as follows:

Change in absorbance at 340 nm = sample absorbance—Blank I absorbance—Blank II absorbance+absorbance of 0.1 ml of NAD-ADH in 0.9 ml of glycine buffer.

The ethanol produced during various periods of incubation, due to the enzymatic hydrolysis of TrEE is calculated from the above value, using the change in absorbance at 340 nm values obtained for the ethanol standard above. The esterase activity of the enzyme-like modified protein prepared according to the present invention is calculated from the above values using linear regression analysis, and expressed as one unit=-micromoles of ethanol produced per minute by one gram of enzyme-like modified protein.

The following activities for the enzyme-like modified protein and the control are obtained for the esterase activity of the enzyme-like modified apotryptophanase and holotryptophanase treated to similar procedure.

| | SUBSTRATE L-TrEE (Activity in Units/Gram) |
|---|---|
| Enzyme-like modified protein (EXP2) | 1.5 ± 0.6 |
| Enzyme-like modified protein (EXP1) | 3 ± 2 |
| Modified holotryptophanase reference | −.8 ± .2 |

This illustrates the conversion of a lyase into an enzyme-like modified protein having esterase type hydrolytic activity.

EXAMPLE 9

Aldose-1 epimerase or mutarotase catalyzes the interconversion of the alpha and beta anomers of D-glucose, to produce an equilibrium mixture of 66% beta-(D) glucose and 34% alpha-(D)-glucose. Generation of such an activity from Concanavalin A is achieved by the following procedure using a natural inhibitor of aldose-1 epimerase.

PART A

Partial Denaturation of Concanavalin A by Production of Apo Concanavalin A

Fifty mg. of Concanavalin A -2X (hereinafter Con A) from ICN Nutritional Biochemicals, Cat. No. 101410, Lot 1981, is dissolved in 100 ml of deionized distilled water and the pH of the solution is adjusted to 3.0, by slow addition of 17.4 M acetic acid. This solution is stirred at room temperature for one hour, and then dialyzed against 3.5 liters of 0.001 M ethylene diamine tetra acetic acid disodium salt solution, adjusted to pH 3.0 with 17.4 M acetic acid. After 6 hours of dialysis, the dialysate is changed to 3.5 liters of distilled deionized water, adjusted to pH 3.0 with 17.4 M acetic acid, and the dialysis continued for 15 hours. The above process removes the cofactors, namely $Ca^{+2}$ and $Mn^{+2}$ metal ions, from the native Con A holoprotein to produce a cofactor-free partially denatured apoprotein. Such cofactor removal is reported by J. W. Becker et. al. in *Nature*, 259, 406–409 (1976).

PART B

Addition of Inhibitor

The solution of PART A containing the demetallized cofactor free partially denatured Con A is divided into two 50 ml portions. To one 50 ml portion is added 10 mg of D-mannitol natural inhibitor for aldose-1 epimerase (from Sigma Chemicals, Cat. No. M 4125, Lot 81 F-0517) and the solution stirred for two hours at room temperature. The other 50 ml of apoCon A is simply stirred for two hours, without any added inhibitor as a first control preparation.

PART C

Cross-linking

The partially denatured-inhibitor bound apoCon A solution, and the partially denatured apo Con A control solution are brought to pH 7.0, by the slow addition of 0.1 N NaOH, and cooled to 5° C., by stirring in a refrigerator for 30 minutes. Next, 200 microliters of 8% glutaraldehyde reagent (from Polyscience, Cat. No. 0216) is added to both solutions, and stirring continued for 6 hours at 5° C. The solutions of the partially denatured inhibitor bound apoCon A, and the control apoCon A, are dialyzed against 0.001 M acetate buffer, pH 6.0 for 48 hours, with six changes of the dialysate. The solutions are lyophilized, and stored as powders at −60° C., until assayed for aldose-1 epimerase activity.

In addition to the first reference preparation consisting of partially denatured, non-inhibitor bound apoCon A, a second reference of inhibitor contacted but not partially denatured native Con A holoprotein is also prepared. Fifty mg of native Con A holoprotein is dissolved in 100 ml of distilled deionized water, and to this solution is added 20 mg of D-mannitol inhibitor. The native Con A holoprotein solution is stirred with the D-mannitol inhibitor for two hours, adjusted to pH 7.0 with 0.1 N NaOH, and cross-linked for 6 hours with 400 microliters of 8% glutaraldehyde. The second control Con A holoprotein solution is dialyzed and lyophilized to produce a powder which is stored at −60° C. until assayed for epimerase activity.

A third control comprising a solution of native Con A holoprotein in 0.1 M sodium phosphate buffer, pH 7.8, without any prior treatment is also prepared for assay for epimerase activity.

PART D

Results

The assay for aldose-1 epimerase (or so-called mutarotase) activity is based on the fact that the enzyme glucose oxidase specifically oxidized beta-(D)-glucose to gluconolactone, and has no activity towards alpha-(D)-glucose glucose. Thus, the epimerase activity is established by using alpha-(D)-glucose as the substrate, and measuring the generation of beta-(D)-glucose by coupling with a glucose oxidase-peroxidase assay (PGO) system as disclosed by Kesdan A. S., in *Abstracts 129th Meeting of the ACS*, p-31 C, (1956). The reaction involves the oxidation of beta-(D)-glucose by the enzyme glucose oxidase to gluconolactone and hydrogen peroxide; peroxidase enzyme then transfers from hydrogen to the dye ortho-dianisidine to produce the oxidized dye which has an absorption maximum between 425-460 mu. The increase in the absorption of the oxidized ortho-dianisidine at 450 mu gives the measure of the epimerase activity present.

The following reagents are purchased from Sigma Chemical Company for the assay:

PGO-enzyme (Stock 510-6), each preweighed capsule of this reagent contains 500 units of glucose oxidase, and 100 units of peroxidase, along with buffer salts. Before use, two capsules are dissolved in 50 ml of distilled water.

Ortho-dianisidine hydrochloride (Stock No. 510-50), preweighed vials containing 50 mg of the chromogen dye is dissolved in 20 ml of distilled water.

A combined enzyme-color reagent is prepared by mixing 50 ml of PGO-solution with one ml of the chromogen dye solution.

A standard curve for glucose is constructed as follows: Sigma Chemical Company glucose standard solution (Stock 635-100) containing 5.56 millimoles of glucose per liter is diluted 1 to 100 with distilled deionized water to obtain a standard solution containing 0.0556 micromoles of glucose per milliliter. Aliquots of 50, 100, 150, and 200 microliters of this standard solution are pipetted into clean glass tubes and the volumes are equalized to 200 microliters by adding appropriate volumes of distilled deionized water. A blank tube containing 200 microliters of distilled deionized water is also prepared. To each tube is added 1.3 ml of PGO-color reagent, contents are mixed, on a Vortex mixer, and allowed to stand for 5 minutes at room temperature. The absorbances are measured at 450 mu, in a Cary 15 spectrophotometer.

The assay for epimerase activity present in the epimerase-like modified proteins prepared according to the present invention is as follows: 4 ml of the PGO-chromogen mixture is mixed with 0.1 ml of freshly made dextrose solution (1 m9/ml). The dextrose is obtained from MCB laboratories, and the solution is prepared in 0.1 M sodium phosphate buffer, pH 7.8, just prior to use.

The combined solution of PGO-chromogen-dextrose is pipetted into the sample and reference cell (1.5 ml. each). The cells are placed in the spectrophotometer and absorbance at 450 mu recorded, until a stable baseline is obtained.

The lyophilized epimerase-like modified protein and the three control preparations are dissolved in 0.1 M sodium phosphate buffer, pH 7.8, and centrifuged to obtain a clear supernatant. Aliquots of 50 microliters of this supernatant is introduced into the sample cell containing the PGO reagent and dextrose. The same volume of 0.1 M phosphate buffer, pH 7.8 is added to the reference cell containing also the PGO reagent and dextrose. The cells are covered with pieces of parafilm, and the contents are mixed. After 5 minutes, the increase in the absorbance of the sample versus the reference is recorded for several minutes. The epimerase activity is calculated from the absorbance change per minute and using the values for standard concentrations and the method disclosed in Example 1, above.

Protein concentrations for the epimerase-like modified protein and the three control preparations are determined by measuring the absorbance at 280 mu, and using the standard absorbance value of a 1% Con A solution as 12.4 as disclosed by Kirschenbaum D. M., in *Int. J. Protein Res.* 4, 63-73 (1972).

The assay results are as follows:

|  | Substrate Alpha-(D)- glucose (activity in U/gram) |
| --- | --- |
| Epimerase-like modified protein | 10.0 |
| Control One - Partially denatured- not inhibitor bound Con A | 0.0 |
| Control Two - Native Con A contacted with inhibitor and cross- linked not partially denatured | 0.0 |
| Control Three - Native Con A | 0.0 |

The above results demonstrate that the epimerase-like modified protein produced according to the present invention exhibits enzymatic activity with respect to the conversion of alpha-(D)-glucose into beta-(D)-glucose.

No such activity is detected in the native Con A holoprotein, Control Three.

No such activity is detected in the Con A contacted with inhibitor, cross-linked but not partially denatured, Control Two.

No such activity is detected in the Con A simply partially denatured, Control One.

This illustrates the conversion of one genus of protein, namely, a non-enzymatic Con A holoprotein starting material into another genus of protein, namely, an enzymatically active epimerase-like modified protein of the isomerase enzyme group.

EXAMPLE 10

DEMONSTRATION OF ABSENCE OF GLUCOSE ISOMERASE ACTIVITY IN APOENZYME OF GLUCOSE OXIDASE

PART A

Partial Denaturation of Glucose Oxidase to Produce Apo Glucose Oxidase

Glucose oxidase is a flavin containing glycoprotein which catalyzes the oxidation of glucose to gluconic acid. The glycoprotein contains two moles of flavin-adenine dinucleotide (FAD) per mole of enzyme, and has a molecular weight of 160,000 consisting of two identical subunits. The apoenzyme of glucose oxidase prepared by the acid-ammonium sulfate method has a molecular weight of 160,000. This is reported in an article by: Tsuge, H., Natsuaki, O., and Ohashi, K., *J. Biochemistry*, 78, 835–843, (1975). They also showed that apoenzyme prepared by the acid-ammonium sulfate method has no native glucose oxidase activity, but that incubating the apoenzyme with an excess of FAD, the natural holoenzyme oxidase activity is regenerated.

According to an article by: Swoboda, B. E. P., *Biochim. Biophys. ACTA*, 175, pages 380–387, (1969)., "It has been proposed that the apoenzyme exists in two forms, $P_1$ and $P_2$, which are probably in equilibrium with one another. The $P_1$ (80%) has a loose flexible coil structure and a molar frictional ratio of 2.2 at pH 5.6. The $P_2$ form (20%) has a more compact structure and a frictional ratio of 1.2." Thus the structure of glucose oxidase is partially denatured by the removal of the FAD moiety.

The apoenzyme of glucose oxidase used herein is prepared by removing the FAD of glucose oxidase using the method as described in the article: Tsuge, H. and Midsuda, H., *The Journal of Vitaminology.*, 17, 24–31, (1971).

About 200 milligrams of glucose oxidase (type VII) from *Aspergillus niger*, purchased from Sigma Chemical Company, as No. G-2133, Lot 88C-0064, is dissolved in 50 milliliters of distilled deionized water and ammonium sulfate granules are added slowly to bring the solution to 80% of saturation. The glucose oxidase solution is kept at 0° C. during the course of this procedure. The pH of the solution is adjusted to 2.0 with a 4 N HCl solution and allowed to stand for 30 minutes. The resulting precipitate is centrifuged at 27,000 gravity forces for 30 minutes. The yellow supernatant is decanted and the slightly yellowish precipitate is dissolved in 2.5 milliliters of 2.0 M ammonium acetate. The resulting solution is added dropwise to 50 milliliters of acidic-85% saturated ammonium sulfate solution (pH 2.0 adjusted with 4 N HCl). The above treatment is repeated three times so that the supernatant fraction appears colorless.

After repeating the acid ammonium-sulfate precipitation three times, the precipitate is dissolved in 50 milliliters of 0.1 M sodium phosphate buffer, pH 7.0 and dialyzed against 0.01 M sodium phosphate buffer, pH 7.0 for 36 hours using a dialysis tubing having a molecular weight cut off of 12–14,000 daltons. The concentration of the dialyzed apoenzyme is determined in accordance with the teachings of D. M. Kirschenbaum in *Analytical Biochemistry* 82, pages 83–100, 1977. The absorbance at 280 nm is measured as 3.04. Using the absorbance coefficient value of 10.6, the concentration of the solution is about 2.87 milligrams per milliliter.

The activity of the native glucose oxidase and the apoenzyme is determined by the colorimetric determination of hydrogen peroxide produced during the coupled reaction with O-dianisidine and peroxidase. This assay procedure is obtained from the *Worthington Enzyme Manual*, pages 19–20, 1972. The activity is expressed as units/milligram where one unit of glucose oxidase activity is that amount of enzyme liberating one micromole of $H_2O_2$ per minute at 25° C. The results of this assay shows that the apoenzyme has only 0.07% of the initial activity of the native glucose oxidase.

PART B

Preparation of Immobilized Model Enzyme Inhibitor Column

A method of purifying this apoenzyme, that is, a method of removing all the native glucose oxidase activity to produce an apo protein totally devoid of activity, is developed in which the dialyzed apoenzyme of PART A is added to a cellobiose inhibitor gel affinity column. The cellobiose inhibitor gel is prepared as described in Example 2. A glass walled chromatography column of about 5.0 centimeters in length and 1.5 centimeters in interior diameter is used in the procedure. To prepare the column for acceptance of the dialyzed apoenzyme, the column is packed about 3.8 centimeters high with immobilized inhibitor, cellobiose gel. After packing the column, it is purged of possible contaminants by washing the column as follows: 200 milliliters of 0.001 M tris-HCl buffer, pH 8.0; 200 milliliters of 0.05 M sodium acetate buffer, pH 5.5; 150 milliliters of 2.0 M guanidine HCl aqueous solution; and finally with 200 milliliters of 0.1 M sodium phosphate buffer, pH 7.0.

PART C

Purification of Dialyzed Apoenzyme of Glucose Oxidase

The column of PART B is purged with a flowing stream of 0.1 M sodium phosphate buffer, pH 7.5, flowing at 1.5 milliliters per minute. Five milliliters of dialyzed apoenzyme of PART A is injected at the head of the column. The eluant from the column is monitored at 280 nm. When that portion of the apoenzyme not binding to the immobilized inhibitor eluted from the column, it is collected and determined to contain 10.8 milligrams of apoenzyme by using the method of D. M. Kirschenbaum described above. Accordingly, about 3.5 milligrams of apoenzyme is bound to the inhibitor column on one exposure to the column.

A portion of the apoenzyme not binding to the cellobiose gel is assayed for glucose oxidase activity by the colorimetric determination of hydrogen peroxide produced during the coupled reaction of O-dianisidine and peroxidase described above. All of the glucose oxidase activity (expressed as total units) in the two milliliter sample of dialyzed apoenzyme added to the column is present in the portion of the apoenzyme not binding to the column. Therefore, the apoenzyme still bound to the column has no glucose oxidase activity.

PART D

Collection of the Purified Apoenzyme

A 0.05 M glycine—NaOH buffer, pH 9.5 is pumped through the column at 1.5 milliliters per minute. After about 5 minutes, purified apoenzyme of glucose oxidase began eluting the column. Forty-eight milliliters of eluant is collected before the purified apoenzyme stopped eluting. The absorbance at 280 nm is determined as in PART A to be 0.067, thus, about 3.0 milligrams of apoenzyme is found to be collected.

PART E

Results

A portion of the eluant collected in PART D is analyzed for glucose isomerase enzymatic activity as follows: The assay is done colorimetrically using a Sigma Glucose Diagnostic Kit No. 510-A by measuring glucose content as a function of time. The procedure is based upon the coupled enzymatic reactions of glucose oxidase and peroxidase and O-dianisidine as a chromogen. The intensity of the brown color measured at 450 nm is proportional to the original glucose concentration.

The purified apoenzyme assay solution is prepared by mixing 2.0 milliliters of purified apoenzyme of PART D, collected at pH 9.5 and 1.5 milliliters of 0.2 M sodium phosphate buffer, pH 7.5 with 0.5 milliliter of 0.2 M beta-D fructose dissolved in distilled deionized water.

The control solution No. 1 is prepared by mixing 2.0 milliliters of purified apoenzyme of PART D, collected at pH 9.5 and 1.5 milliliter of 0.2 M sodium phosphate buffer, pH 7.5 with 0.5 milliliter of distilled deionized water.

The control solution No. 2 is prepared by mixing 2.0 milliliters of 0.05 M glycine-NaOH buffer, pH 9.5 and 1.5 milliliters of 0.2 M sodium phosphate buffer, pH 7.5 with 0.5 milliliter of 0.2 M beta-D fructose in distilled deionized water.

The final pH of both blanks and assay solution is 8.0.

The assay solution, control No. 1 and control No. 2 is placed in a 37° C. water bath and allowed to gently shake. After incubating at 37° C. for 10 minutes, 20 minutes, 30 minutes and 60 minutes; 0.5 milliliter of each solution is removed and added to 1.0 milliliter of a solution containing glucose oxidase, peroxidase and O-dianisidine (PGO). The PGO reaction is allowed to proceed to completion in approximately 30 minutes at 37° C., and then the absorbance at 450 nm is measured on a Cary 14 Spectrophotometer.

For each time interval, the change in absorbance is calculated by subtracting the absorbance of control No. 1 and control No. 2 from the absorbance of the assay solution and then adding the absorbance of 1.0 milliliter of PGO solution added to 0.5 milliliter of buffer (one-half glycine-NaOH buffer and one-half sodium phosphate buffer)., i.e. Assay solution—Control No. 1—Control No., 2 +PGO and buffer=change in absorbance.

The absorbance for each time interval listed above is calculated to be zero.

The results show that the purified apoenzyme collected in PART D exhibits no measurable glucose isomerase enzymatic activity.

We claim:

1. A process for chemically altering the substrate specificity of a cofactor containing native holoprotein to produce a predetermined cofactorless ensyme-like modified protein comprising the steps of:
    selecting an enzyme to be modeled, said enzyme having an enzymatic activity different from said native holoprotein;
    partially denaturing a cofactor containing native holoprotein by removing the cofactor therefrom by contacting the holoprotein with a cofactor removal agent to produce a partially denatured apoprotein;
    cross-linking said partially denatured apoprotein in the presence of a competitive inhibitor of said model enzyme with a cross-linking agent to produce an enzyme-like modified protein having the catalytic activity of said model enzyme.

2. The product of the process of claim 1.

3. A process for chemically altering the substrate specificity of a cofactor containing native holoprotein to produce a predetermined enzyme-like modified protein comprising the steps of:
    selecting an enzyme to be modeled, said enzyme having an enzymatic activity different from said native holoprotein;
    partially denaturing a cofactor containing native holoprotein by removing the cofactor therefrom by contacting the holoprotein with a cofactor removal agent to produce a partially denatured apoprotein;
    contacting said partially denatured apoprotein with a competitive inhibitor of said selected model enzyme to form a partially denatured apoprotein-inhibitor complex;
    contacting said partially denatured apoprotein-inhibitor complex with a solid support for a time sufficient and at a temperature sufficient to absorb and immobilize said partially denatured apoprotein-inhibitor complex on said solid support; and
    cross-linking said absorbed, immobilized partially denatured apoprotein-inhibitor complex with a cross-linking agent to produce an enzyme-like modified protein having the catalytic activity of said model enzyme.

4. The process defined in claim 3 wherein said solid support is a ceramic oxide.

5. The process defined in claim 3 wherein said solid support is an organic polymer support.

6. The product of the process of claim 3.

7. A process for chemically altering the substrate specificity of a cofactor containing native holoprotein to produce a predetermined enzyme-like modified protein comprising the steps of:
    selecting an enzyme to be modeled, said enzyme having an enzymatic activity different from said native holoprotein;
    absorbing a native holoprotein onto a solid support to immobilize said native holoprotein on said solid support;
    partially denaturing said immobilized holoprotein by removing the cofactor therefrom by contacting the holoprotein with a cofactor removal agent to produce a partially denatured, immobilized apoprotein;
    contacting said partially denatured, immobilized apoprotein with a competitive inhibitor of said selected model enzyme; and
    cross-linking said partially denatured immobilized apoprotein in the presence of said inhibitor of said model enzyme with a cross-linking agent to produce an enzyme-like modified protein having the catalytic activity of said model enzyme.

8. The process claimed in claim 7 wherein said solid support is a ceramic oxide.

9. The process claimed in claim 7 wherein said solid support is an organic polymer support.

10. The product of the process of claim 7.

11. A process for chemically altering the substrate specificity of a cofactor containing native holoprotein to produce a predetermined enzyme-like modified protein comprising the steps of:
    selecting an enzyme to be modeled, said enzyme having an enzymatic activity different from said native holoprotein;
    immobilizing a competitive inhibitor of said model enzyme on a solid support;
    partially denaturing a cofactor containing native holoprotein by removing the cofactor therefrom by contacting the holoprotein with a cofactor removal agent to produce a partially denatured apoprotein;
    contacting said partially denatured apoprotein with said immobilized inhibitor to form a partially denatured apoprotein-immobilized inhibitor complex; and cross-linking said partially denatured apoprotein while in contact with said immobilized inhibitor with a cross-linking agent to produce an enzyme-like modified protein having the biological activity of said model enzyme.

12. The process of claim 11 wherein said support is a ceramic oxide support.

13. The process of claim 11 wherein said support is an organic polymer support.

14. The product of the process of claim 11.

15. The process defined in claim 1 wherein said native holoprotein is selected from the group consisting of concanavalin A, glucose oxidase, and tryptophanase, said enzyme to be modeled is selected from the group consisting of glucose isomerase, esterase, and aldose-1 epimerase, and said inhibitor is selected from the group consisting of cellobiose, mannitol, and indole.

16. The process defined in claim 3 wherein said native holoprotein is selected from the group consisting of concanavalin A, glucose oxidase, and tryptophanase, said enzyme to be modeled is selected from the group consisting of glucose isomerase, esterase, and aldose-1 epimerase, and said inhibitor is selected from the group consisting of cellobiose, mannitol, and indole.

17. The process defined in claim 7 wherein said native holoprotein is selected from the group consisting of concanavalin A, glucose oxidase, and tryptophanase, said enzyme to be modeled is selected from the group consisting of glucose isomerase, esterase, and aldose-1 epimerase, and said inhibitor is selected from the group consisting of cellobiose, mannitol, and indole.

18. The process defined in claim 11 wherein said native holoprotein is selected from the group consiting of concanavalin A, glucose oxidase, and tryptophanase, said enzyme to be modeled is selected from the group consisting of glucose isomerase, esterase, and aldose-1 epimerase, and said inhibitor is selected from the group consisting of cellobiose, mannitol, and indole.

* * * * *